(12) United States Patent
Hlavinka et al.

(10) Patent No.: US 7,094,197 B2
(45) Date of Patent: Aug. 22, 2006

(54) METHOD FOR FLUID SEPARATION DEVICES USING A FLUID PRESSURE BALANCED CONFIGURATION

(75) Inventors: Dennis J Hlavinka, Arvada, CO (US); Thomas J. Felt, Boulder, CO (US)

(73) Assignee: Gambro, Inc., Lakewood, CO (US)

( * ) Notice: Subject to any disclaimer, the term of this patent is extended or adjusted under 35 U.S.C. 154(b) by 184 days.

(21) Appl. No.: 10/709,079

(22) Filed: Apr. 12, 2004

(65) Prior Publication Data

US 2004/0185998 A1    Sep. 23, 2004

Related U.S. Application Data

(62) Division of application No. 10/005,431, filed on Nov. 2, 2001, now Pat. No. 6,773,389.

(60) Provisional application No. 60/245,282, filed on Nov. 2, 2000.

(51) Int. Cl.
*B01D 21/26* (2006.01)

(52) U.S. Cl. .......................................... 494/37; 494/45

(58) Field of Classification Search ................. 494/37, 494/41, 42, 45, 60, 63, 67, 81; 422/72; 210/781, 210/782, 787; 604/6.01, 6.02, 6.03, 6.04, 604/6.05, 6.06
See application file for complete search history.

(56) References Cited

U.S. PATENT DOCUMENTS

| | | |
|---|---|---|
| 3,145,713 A | 8/1964 | Latham, Jr. |
| 3,519,201 A | 7/1970 | Eisel et al. |
| 3,655,123 A | 4/1972 | Judson et al. |
| 3,737,096 A | 6/1973 | Jones et al. |
| 3,748,101 A | 7/1973 | Jones et al. |
| 3,825,175 A | 7/1974 | Sartory |
| 3,880,592 A | 4/1975 | Kelly et al. |
| 3,955,755 A | 5/1976 | Breillatt, Jr. et al. |
| 3,986,442 A | 10/1976 | Khoja et al. |
| 4,007,871 A | 2/1977 | Jones et al. |
| 4,010,894 A | 3/1977 | Kellogg et al. |
| 4,018,304 A | 4/1977 | Lolachi et al. |
| 4,059,108 A | 11/1977 | Latham, Jr. |

(Continued)

FOREIGN PATENT DOCUMENTS

DE    26 58 926    12/1976

(Continued)

OTHER PUBLICATIONS

D. W. Schoendorter: Automation in Apheresis, pp. 129-146 (undated, in use one year prior to filing).

(Continued)

*Primary Examiner*—David Sorkin
(74) *Attorney, Agent, or Firm*—John R. Merkling; Edna M. O'Connor; Laura Arciniegas

(57) ABSTRACT

A method for separating a composite fluid into components in a centrifugal fluid separation system. The system includes a rotor that has a composite fluid containment area, an inlet channel, a peripheral separation channel, outlet channels and separated component collection areas, which together form a processing area. The separation channel may be semi-spiraled. The inlet channel may connect to the center of the separation channel and an outlet channel may connect to each end of the separation channel. The outlet channels have different heights. The ends of the separation channels may have different heights. The separation channels may have extensions. The rotor may have multiple processing areas. The collection areas may be pockets slanted radially outwardly and downwardly. A motor may produce a rotating magnetic field, which co-acts with a magnetically reactive material in the rotor. A disposable bag and tubing system may be used in a processing area of the rotor.

22 Claims, 23 Drawing Sheets

U.S. PATENT DOCUMENTS

| | | |
|---|---|---|
| 4,086,924 A | 5/1978 | Latham, Jr. |
| 4,094,461 A | 6/1978 | Kellogg et al. |
| 4,108,353 A | 8/1978 | Brown |
| 4,109,852 A | 8/1978 | Brown et al. |
| 4,109,854 A | 8/1978 | Brown |
| 4,109,855 A | 8/1978 | Brown et al. |
| 4,111,356 A | 9/1978 | Boggs et al. |
| 4,113,173 A | 9/1978 | Lolachi |
| 4,114,802 A | 9/1978 | Brown et al. |
| 4,120,448 A | 10/1978 | Cullis |
| 4,120,449 A | 10/1978 | Brown et al. |
| 4,146,172 A | 3/1979 | Cullis et al. |
| 4,164,318 A | 8/1979 | Boggs |
| 4,185,629 A | 1/1980 | Cullis et al. |
| 4,187,979 A | 2/1980 | Cullis et al. |
| 4,191,182 A | 3/1980 | Popovich et al. |
| 4,194,684 A | 3/1980 | Boggs |
| 4,216,770 A | 8/1980 | Cullis et al. |
| 4,245,383 A | 1/1981 | Boggs |
| 4,303,193 A | 12/1981 | Latham, Jr. |
| 4,304,357 A | 12/1981 | Schoendorfer |
| 4,330,080 A | 5/1982 | Mathieu |
| 4,332,351 A | 6/1982 | Kellogg et al. |
| 4,379,452 A | 4/1983 | DeVries |
| 4,386,730 A | 6/1983 | Mulzet |
| 4,387,848 A | 6/1983 | Kellogg et al. |
| 4,402,680 A | 9/1983 | Schoendorfer |
| 4,416,654 A | 11/1983 | Schoendorfer et al. |
| 4,416,778 A | 11/1983 | Rogers |
| 4,417,884 A | 11/1983 | Schoendorfer et al. |
| 4,421,503 A | 12/1983 | Latham, Jr. et al. |
| 4,425,112 A | 1/1984 | Ito |
| 4,430,072 A | 2/1984 | Kellogg et al. |
| 4,435,293 A | 3/1984 | Graham, Jr. et al. |
| 4,436,631 A | 3/1984 | Graham, Jr. et al. |
| 4,439,178 A | 3/1984 | Mulzet |
| 4,447,221 A | 5/1984 | Mulzet |
| 4,464,167 A | 8/1984 | Schoendorfer et al. |
| 4,482,342 A | 11/1984 | Lueptow et al. |
| 4,526,515 A | 7/1985 | DeVries |
| 4,531,932 A | 7/1985 | Luppi et al. |
| 4,557,719 A | 12/1985 | Neumann et al. |
| 4,610,846 A | 9/1986 | Martin |
| 4,636,193 A | 1/1987 | Cullis |
| 4,637,813 A | 1/1987 | DeVries |
| 4,647,279 A | 3/1987 | Mulzet et al. |
| 4,670,147 A | 6/1987 | Schoendorfer et al. |
| 4,675,106 A | 6/1987 | Schoendorfer et al. |
| 4,675,117 A | 6/1987 | Neumann et al. |
| 4,696,666 A | 9/1987 | Rice, Jr. |
| 4,708,712 A | 11/1987 | Mulzet |
| 4,713,176 A | 12/1987 | Schoendorfer et al. |
| 4,734,089 A | 3/1988 | Cullis |
| 4,738,655 A | 4/1988 | Brimhall et al. |
| 4,740,313 A | 4/1988 | Schoendorfer et al. |
| 4,753,729 A | 6/1988 | Schoendorfer et al. |
| 4,755,300 A | 7/1988 | Fischel et al. |
| 4,776,964 A | 10/1988 | Schoendorfer et al. |
| 4,790,807 A | 12/1988 | Neumann et al. |
| 4,804,363 A | 2/1989 | Valeri |
| 4,806,247 A | 2/1989 | Schoendorfer et al. |
| 4,816,151 A | 3/1989 | Schoendorfer et al. |
| 4,834,890 A | 5/1989 | Brown et al. |
| 4,850,995 A | 7/1989 | Tie et al. |
| 4,850,998 A | 7/1989 | Schoendorfer |
| 4,851,126 A | 7/1989 | Schoendorfer |
| 4,869,812 A | 9/1989 | Schoendorfer et al. |
| 4,879,040 A | 11/1989 | Prince et al. |
| 4,911,833 A | 3/1990 | Schoendorfer et al. |
| 4,919,817 A | 4/1990 | Schoendorfer et al. |
| 4,934,995 A | 6/1990 | Cullis |
| 4,935,002 A | 6/1990 | Gordon |
| 4,940,543 A | 7/1990 | Brown et al. |
| 4,943,273 A | 7/1990 | Pages |
| 4,944,883 A | 7/1990 | Schoendorfer et al. |
| 4,968,295 A | 11/1990 | Neumann |
| 4,983,158 A | 1/1991 | Headley |
| 4,990,132 A | 2/1991 | Unger et al. |
| 5,006,103 A | 4/1991 | Bacehowski et al. |
| 5,034,135 A | 7/1991 | Fischel |
| 5,053,121 A | 10/1991 | Schoendorfer et al. |
| 5,053,127 A | 10/1991 | Schoendorfer et al. |
| 5,061,381 A | 10/1991 | Burd |
| 5,104,526 A | 4/1992 | Brown et al. |
| RE33,924 E | 5/1992 | Valeri |
| 5,114,396 A | 5/1992 | Unger et al. |
| 5,135,667 A | 8/1992 | Schoendorfer |
| 5,147,290 A | 9/1992 | Jonsson |
| 5,171,456 A | 12/1992 | Hwang et al. |
| 5,186,844 A | 2/1993 | Burd et al. |
| 5,188,583 A | 2/1993 | Guigan |
| 5,194,145 A | 3/1993 | Schoendorfer |
| 5,217,426 A | 6/1993 | Bacehowski et al. |
| 5,217,427 A | 6/1993 | Cullis |
| 5,260,598 A | 11/1993 | Brass et al. |
| 5,275,731 A | 1/1994 | Jahn |
| 5,281,342 A | 1/1994 | Biesel et al. |
| 5,295,953 A | 3/1994 | Richard et al. |
| 5,298,171 A | 3/1994 | Biesel |
| 5,370,802 A | 12/1994 | Brown |
| 5,376,263 A | 12/1994 | Fischel |
| 5,405,308 A | 4/1995 | Headley et al. |
| 5,421,812 A | 6/1995 | Langley et al. |
| 5,445,593 A | 8/1995 | Biesel et al. |
| 5,464,534 A | 11/1995 | Fischel |
| 5,494,592 A | 2/1996 | Latham, Jr. et al. |
| 5,571,068 A | 11/1996 | Bacehowski et al. |
| 5,605,842 A | 2/1997 | Langley et al. |
| 5,607,579 A | 3/1997 | Latham, Jr. et al. |
| 5,607,830 A | 3/1997 | Biesel et al. |
| 5,611,997 A | 3/1997 | Langley et al. |
| 5,614,106 A | 3/1997 | Payrat et al. |
| 5,651,766 A | 7/1997 | Kingsley et al. |
| 5,653,887 A | 8/1997 | Wahl et al. |
| 5,674,173 A | 10/1997 | Hlavinka et al. |
| 5,702,357 A | 12/1997 | Bainbridge et al. |
| 5,704,888 A | 1/1998 | Hlavinka et al. |
| 5,704,889 A | 1/1998 | Hlavinka et al. |
| 5,722,926 A | 3/1998 | Hlavinka et al. |
| 5,723,050 A | 3/1998 | Unger et al. |
| 5,728,060 A | 3/1998 | Kingsley et al. |
| 5,733,253 A | 3/1998 | Headley et al. |
| 5,738,644 A | 4/1998 | Holmes et al. |
| 5,738,792 A | 4/1998 | Schoendorfer |
| 5,779,660 A | 7/1998 | Kingsley et al. |
| 5,783,085 A | 7/1998 | Fischel |
| 5,792,038 A | 8/1998 | Hlavinka |
| 5,853,382 A | 12/1998 | Kingsley et al. |
| 5,876,321 A | 3/1999 | Hlavinka et al. |
| 5,882,289 A | 3/1999 | Sakota et al. |
| 5,885,239 A | 3/1999 | Headley et al. |
| 5,904,355 A | 5/1999 | Powers |
| 5,939,319 A | 8/1999 | Hlavinka et al. |
| 5,951,877 A | 9/1999 | Langley et al. |
| 5,954,626 A | 9/1999 | Hlavinka |
| 6,007,509 A | 12/1999 | Kingsley et al. |
| 6,019,742 A | 2/2000 | Headley et al. |
| 6,039,711 A | 3/2000 | Headley et al. |
| 6,053,856 A | 4/2000 | Hlavinka |
| 6,062,078 A | 5/2000 | Meisberger |
| 6,074,335 A | 6/2000 | Headley et al. |
| 6,099,491 A | 8/2000 | Headley et al. |
| 6,102,883 A | 8/2000 | Kingsley et al. |
| 6,200,287 B1 | 3/2001 | Keller et al. |

| | | |
|---|---|---|
| 6,221,315 B1 | 4/2001 | Giesler et al. |
| 6,261,217 B1 | 7/2001 | Unger et al. |
| 6,273,849 B1 | 8/2001 | Scherer |
| 6,277,060 B1 | 8/2001 | Neumann |
| 6,280,375 B1 | 8/2001 | Meisberger et al. |
| 6,296,602 B1 | 10/2001 | Headley |
| 6,315,707 B1 | 11/2001 | Smith et al. |
| 6,319,471 B1 | 11/2001 | Langley et al. |
| 6,322,488 B1 | 11/2001 | Westberg et al. |
| 6,325,775 B1 | 12/2001 | Thom et al. |
| 6,334,842 B1 | 1/2002 | Hlavinka et al. |
| 6,736,768 B1 * | 5/2004 | Felt et al. .................... 494/60 |
| 6,773,389 B1 * | 8/2004 | Hlavinka et al. ............ 494/60 |
| 2004/0164032 A1 * | 8/2004 | Felt et al. ................... 210/787 |

FOREIGN PATENT DOCUMENTS

| | | |
|---|---|---|
| EP | 0096217 | 2/1983 |
| EP | 0214803 | 3/1987 |
| EP | 1043072 | 10/2000 |
| JP | 55086552 | 6/1980 |
| WO | PCT/US95/13447 | 4/1996 |
| WO | PCT/US96/03018 | 12/1996 |
| WO | PCT/US00/06561 | 9/2000 |

OTHER PUBLICATIONS

International Search Report for Corresponding PCT ApplicationPCT/US01/46940.

* cited by examiner

METHOD FOR FLUID SEPARATION DEVICES USING A FLUID PRESSURE BALANCED CONFIGURATION

CROSS REFERENCE TO RELATED APPLICATIONS

This case is a divisional of U.S. application Ser. No. 10/005,431, filed Nov. 2, 2001, now U.S. Pat. No. 6,773,389, which claims the benefit of U.S. Provisional application Ser. No. 60/245,282 filed on Nov. 2, 2000.

BACKGROUND OF INVENTION

The present invention is directed generally to centrifugal fluid separation devices and more particularly involves a pressure driven and/or balanced separation device preferably having a simplified disposable tubing and bag set used with a loopless, rotating sealless rotor.

A number of fluid separation devices have been known and various models are currently available for the separation of blood or other composite fluids into the various component elements thereof. For example, a variety of centrifugal machines are available for separating blood into component elements such as red blood cells, platelets and plasma, among others.

Centrifugation for such purposes has come in many forms in both continuous and batch types. For example, in the widely used process known as continuous centrifugation, as generally opposed to batch process centrifugation, a continuous input of a composite fluid is flowed into the separation device or chamber while at the same time the components of that composite fluid are substantially continuously separated and these separated components are usually then also substantially continuously removed therefrom. Many currently popular forms of such continuous fluid separation devices include loops of entry and exit flow tubing lines connected to the separation centrifuge chamber such that each loop is rotated in a relative one-omega—two-omega ($1\omega$–$2\omega$) relationship to the centrifuge chamber itself so that the tubing lines will remain free from twisting about themselves.

An alternative form of tubing line connection to a continuous centrifugal separation device is also available in the art which does not have such a loop, but which instead requires one or more rotating seals at the respective connections of the tubing lines to the centrifuge separation chamber, again to maintain the tubing lines free from twisting.

Batch-type centrifugation, on the other hand, usually involves separation of a composite fluid such as whole blood in a closed container, often a deformable bag, followed by a usually complicated process of automated and/or manual expression of one or more of the separated components out of the separation container or bag. A great deal of control, either automated, such as by optical interface detection, or by a diligent human operator watching a moving interface, is required with such previous batch-type processes. Indeed, various means and methods have been used in prior centrifugal separation devices, both continuous and batch, for driving fluid flow and maintaining desirable interface position control between the component elements being separated thereby. For example, as mentioned, various optical feedback methods and devices have been employed in the art. Various pumping and valving arrangements are also used in various of these and other arrangements. Alternative relatively automatic volume flow and density relationship interface controls have also been used; for example, in a continuous system by the disposition of control outlet ports in strategic locations relative to the separated component outlet ports. Nevertheless, many facets of these prior separation devices, though satisfactorily productive, may provide certain features which are less efficient than a desired optimum. For example, centrifugal separation devices using loops of tubing lines rotated in the above-described $1\omega$–$2\omega$ relationship with the centrifuge separation chamber require significant, usually substantially large drive mechanisms which thereby mandate that each such entire device then also be necessarily of a relatively large scale. Rotating seal devices, on the other hand, require intricate and often operationally problematic rotating seal structures. Still further, prior fluid drive and/or interface control systems have generally been either overly complex, as in the case of most of the optical control models, and/or automatic volume flow/density controls may not be entirely efficient in separation due to the usually inherent re-mixing of some quantities of the centrifugally separated components.

Hence, substantial desiderata remain to provide more highly efficient centrifugal separation devices in terms of increased efficiency fluid flow drive and separation interface controls; reduced rotor drive mechanization, quantity and/or scale; and/or reduced seal need and/or intricacy. It is toward any one or more of these or other goals as may be apparent throughout this specification that the present invention is directed.

SUMMARY OF INVENTION

The present invention is directed generally to centrifugal fluid separation devices and/or systems for use in centrifugally separating composite fluids into the component elements thereof. Such centrifugal separation systems include unique centrifugal rotor and rotor/fluid container combinations in which each rotor, preferably with a plurality of containers positioned therein, may together be disposed in a freely rotatable disposition relative to the rotational drive unit. Freely rotatable indicates loopless and rotating sealless as well as the preference that the rotors may be magnetically or otherwise non-invasively driven. A totally closed system may thus also be preferably provided hereby with simple sterilization and disposability of the fluid container/tubing combination and/or the rotor.

Each rotor has a substantially central composite fluid receiving/containing area, at least one component collection area and at least one fluid flow channel defined therein. In a preferred embodiment, a composite fluid to be separated into component parts may then be delivered to the fluid receiving or containment area preferably in a composite fluid container or bag. Then, under centrifuge conditions, the composite fluid may travel from the composite fluid container through a radial fluid inlet channel to a circumferential fluid separation channel where under subjection to centrifugal forces, the composite fluid may be separated into respective components. These components may then travel through respective circumferential channel portions to respective component collection areas where they are preferably collected in collection containers or bags. These separated fluids may then be removed from the separation device in or from the collection bag or bags for storage, further processing or may then be returned to the donor. The composite fluid is preferably whole blood, and the respective components may then be plasma and red blood cells (RBCs), although buffy coats and/or platelets, among others, may also be harvested herewith.

The respective circumferential channel portions preferably include and/or are connected with first and second fluid outlet channel portions through which the separated components may flow to the respective collection areas. These first and second outlet channels preferably have respective first and second outlets which are preferably located at relative radial positions that are selected to be related to each other so as to provide a substantial hydraulic or hydrostatic fluid pressure balance between the outlets for the respective separated fluids flowing therethrough. Such a fluid pressure balance preferably controls the desired location of the interface between the separated fluid components within the circumferential separation channel. The preferred outlet channel height relationship which provides this hydraulic balance may be derived from the general hydrostatic equation $\rho_2 g_2 h_2 = \rho_3 g_3 h_3$ wherein the height or radial distance of the first outlet channel is $h_2$, and the height or radial distance of the second outlet channel is $h_3$. These relative lengths, $h_2$ and $h_3$, may then be selected so as to provide the appropriate preferred pressure balance given a separable composite fluid to be flowed in separated fluid component parts therethrough. The other variables in the above equation are either fluid dependent, see e.g., $\rho_2$ and $\rho_3$ which represent the respective densities of the separated fluids in the first and second outlet channels, or are otherwise relatively non-selectable and/or for the most part not as consequential or are relatively non-governing in the general equation; e.g., the $g_2$ and $g_3$ variables are gravitational acceleration values representing the respective average g value in each of the two columns, which may be a similar, if not a substantially equal value (i.e., even though there is likely a distinction, $g_2$ may generally vary a relatively small amount from $g_3$) in normal operation. Hence, however, the dominant driving, selectable differences will be in the relative heights $h_2$ and $h_3$ which may simply be chosen to accommodate for any differences in the other terms, $\rho$ or g.

Thus, for a composite fluid such as whole blood, where the respective densities of the separable component parts, e.g., plasma and RBCs, are known (within sufficiently controllable ranges), then the respective heights, $h_2$ and $h_3$ may be chosen to appropriately set the location of the interface of separated components therebetween. This interface will thus remain where desired, preferably in the separation channel notwithstanding a substantially continuous inflow of composite fluid to be separated and a substantially continuous outflow of separated components. Note, although a radial direction is preferred for the measurement of these "heights" from a reference circle inward toward the central axis; however, the channels (inlet and outlet) need not be disposed on a radial path. Non-radial and circuitous channel paths may also be effective and provide the pressure drive and balance relationships described herein. Also, the reference line or circle from which the "heights" may be measured may be arbitrary but is preferably within the fluid pathway and here is described relative to the heavier phase separated component (e.g., RBC) outlet from the peripheral channel.

Other similarly derived relationships of interest particularly relative to the dynamic forcing of the fluid flow in this invention, among others, are also involved in the systems of the present invention. For example, a further preferred aspect of the present invention involves a preferred relationship between the outlet fluid pressure term(s) and the inlet pressure term, particularly as these are impacted by the selection of the outlet channel heights or lengths $h_2$ and $h_3$ as described above as well as the inlet channel height or length $h_1$. Here, the fluid will flow in a continuous forward fashion so long as the inlet fluid pressure term $\rho_1 g_1 h_1$ is at least greater than either of the outlet fluid pressure terms $\rho_2 g_2 h_2$ and $\rho_3 g_3 h_3$. In an equation form, this relationship is;

$$\rho_1 g_1 h_1 > \rho_2 g_2 h_2 \text{ or, } \rho_1 g_1 h_1 > \rho_3 g_3 h_3 \rho.$$

This relationship governs a general forcing of the fluid flow in one direction out of the initial receiving/containment area, into the separation channel and from there into the respective component collection areas.

It is to be understood that both the foregoing general description and the following detailed description are exemplary, and are intended merely to provide limited explanation of preferred embodiments of the invention as more broadly claimed. These and further aspects of the present invention will become clearer from the detailed description read in concert with the drawings in which like component elements are referenced therein with like component numbers throughout the several views.

DETAILED DESCRIPTION

A fluid pressure-balanced, loopless, rotating sealless separation device according to the present invention is depicted in the attached drawings and identified by the general reference number 10 therein. Note, the processing of whole blood as the preferred composite fluid is described in the preferred embodiments herein, although other composite fluids may also be processed hereby. Red blood cells (RBCs) and plasma are the primary preferred components described as separated from whole blood herein, although processing for the separation and collection of buffy coats, platelets or white blood cells, among others, may also be accomplished herewith.

Figure 1:
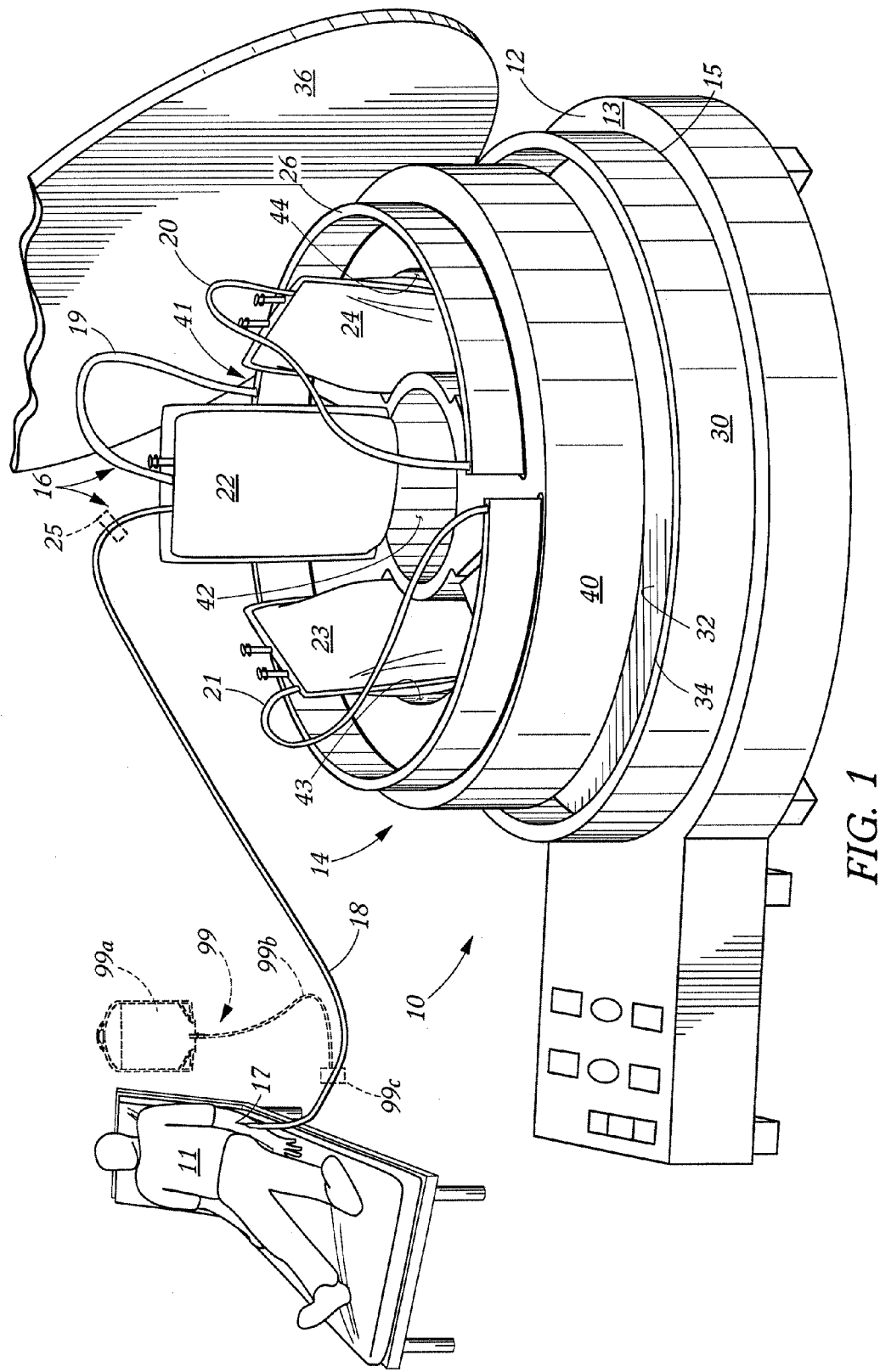
FIG. 1 is a partially exploded isometric view of a separation system of the present invention as may be operably positionable with respective fluid containers and a human donor.

As shown for example in FIG. 1 in relation to a donor 11, a separation device 10 may generally include a motor base 12 and a centrifuge unit 14 with a tubing system 16 having one or more tubing lines 18, 19, 20 and 21 and associated reservoirs or bags 22, 23, and 24. A separate vessel 26 is also shown as part of the tubing system 16. A preferred tubing set 16 with associated lines 18–21, bags 22–24 and vessel 26, is shown in more detail in FIG. 5 (see further description thereof below). These primary component parts and some optional tubing lines and associated optional components will be further described below. Note, the option of using an anticoagulant (A/C) would be preferred, though as an alternative to adding the A/C during collection (see A/C assembly 99 shown schematically in dashed lines in FIG. 1), such anticoagulant may be pre-packaged (not directly shown) in the whole blood collection bag 22, and/or may be later added (after disconnection from the donor) and/or may be determined to be not necessary in a direct donor draw like that shown in Fig.

Figure 15:
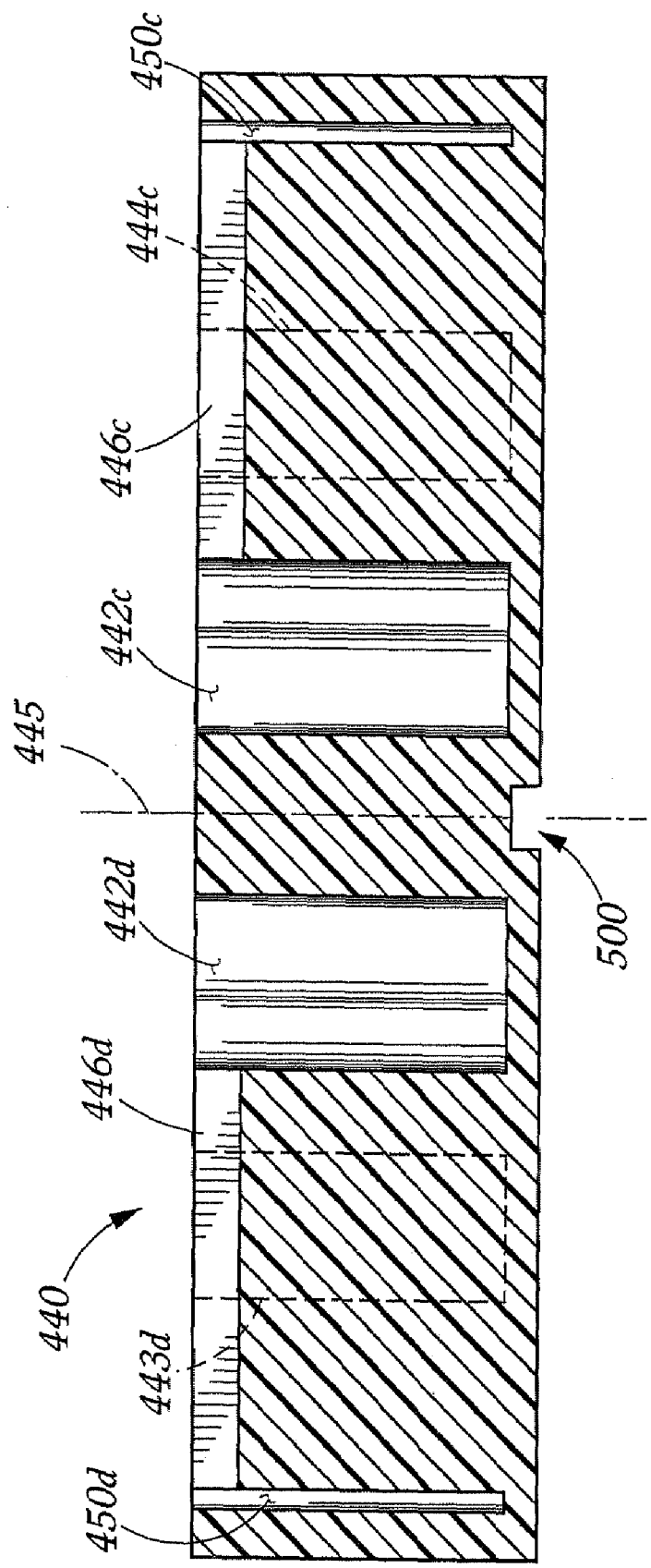
FIG. 15 is a cross-sectional view of the alternative rotor/centrifuge of FIGS. 13 and 14 taken along line 15—15 thereof.

In the preferred embodiment, the motor base 12, which may also be referred to as the drive portion of the separation device 10, is preferably a table-top sized, simply transportable magnetic (or other drive-type) apparatus which in the magnetic embodiment creates a spinning magnetic field. The motor base 12 may create this spinning magnetic field by, for example, physically spinning or rotating one or more magnets disposed therein about a rotational axis defined vertically therethrough, or, the magnetic field could be created alternatively by charging one or more magnets, or electromagnetic coils, in a controlled rotational sequence as is known generally in the industry. Other alternative drive mechanisms may also be used. In one non-exclusive example, the motor base 12 could have a spindle (not shown) emanating therefrom or a notched protrusion receptacle (also not shown) either of which being adapted to engage with a corresponding spindle receptacle or a notched protrusion (neither shown) disposed in the bottom of the rotor 40 of centrifuge 14 (an exemplary spindle receptacle 500 is shown in FIG. 15, as described below). The motor base 12 would then spin its corresponding member to thereby impart, through the mechanical engagement, a rotational movement to the rotor 40.

In any case, the centrifuge unit 14, which may also be referred to as the centrifuge portion or part of the separation device 11, is preferably a self-contained and potentially (though not necessarily) disposable unit which readily mates with the motor base 12. A preferred, readily mating relationship is as follows. Motor base 12 is preferably a flat-topped device which generates a spinning magnetic field that emanates out of the flat-top surface 13 thereof. Centrifuge unit 14 then preferably has a substantially flat-bottomed portion which may be readily placed in operative relationship with or simply set upon the flat-top surface 13 of motor base 12. A preferably flat-bottomed surface 15 of unit 14 may thus be disposed in surface-to-surface contact with the top surface 13 of motor base 12. In the preferred embodiments, this surface-to-surface contact relationship is preferably substantially horizontal. The axis of rotation (see description relative to FIGS. 3 and 4, below) is preferably substantially perpendicular to the flat-top surfacer 3 of base 12 and to the flat-bottomed surface 15 of unit 14 and would thus be substantially vertical in the preferred embodiments shown and described herein.

As depicted in FIG. 1, the centrifuge unit 14 may include an outer housing 30 and an internal rotor 40. In broad terms, the outer housing 30 preferably includes a bottom wall 32 (the exterior face of which being the flat-bottom surface 15 described above), a circumferential wall 34, and a top wall or lid 36. The bottom and circumferential walls 32, 34 are preferably contiguous and may at least partially be integrally conjoined or formed, although they may each be separately-formed elements which are subsequently joined. In either case, these walls may (but not necessarily) form a fluid-tight arrangement. The lid 36 is preferably adapted to be positioned to cover circumferential wall 34 in a potentially fluid-tight arrangement, or may simply cover rotor 40 in a not necessarily fluid tight arrangement to maintain the tubing and bag system 16 therein during rotation. Though preferred in one embodiment, housing 30 need not be fluid-tight in this invention; moreover, it is not necessary in operation so long as the tubing and bag set 16 is fluid-tight, and so long as this set 16 may be sufficiently retained in/on the rotor 40 during rotation as will be described below.

Figure 2:
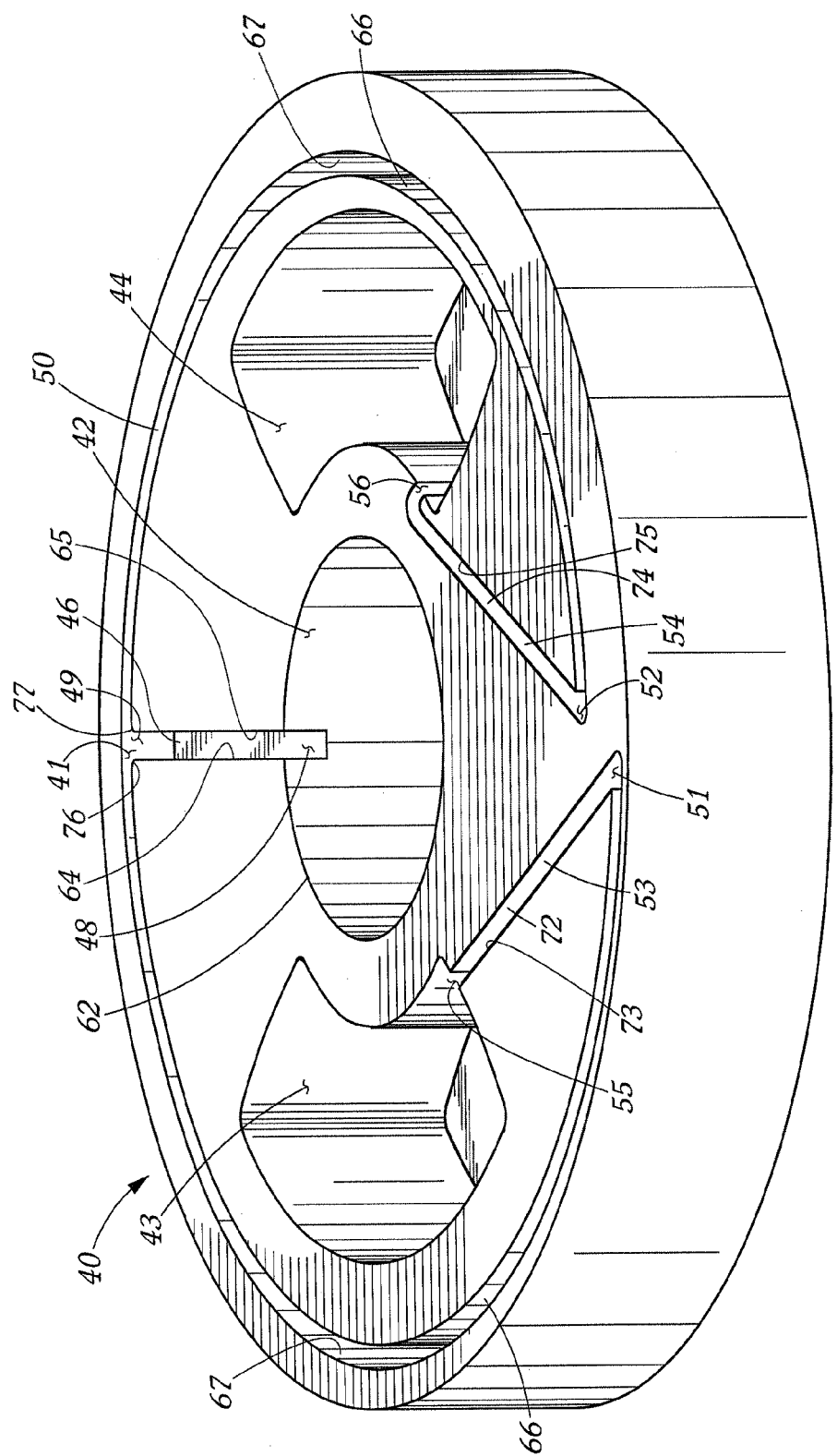
FIG. 2 is an isometric view of a rotor/centrifuge part of a separation device according to the present invention as taken from the embodiment shown in FIG. 1.
Figure 3:
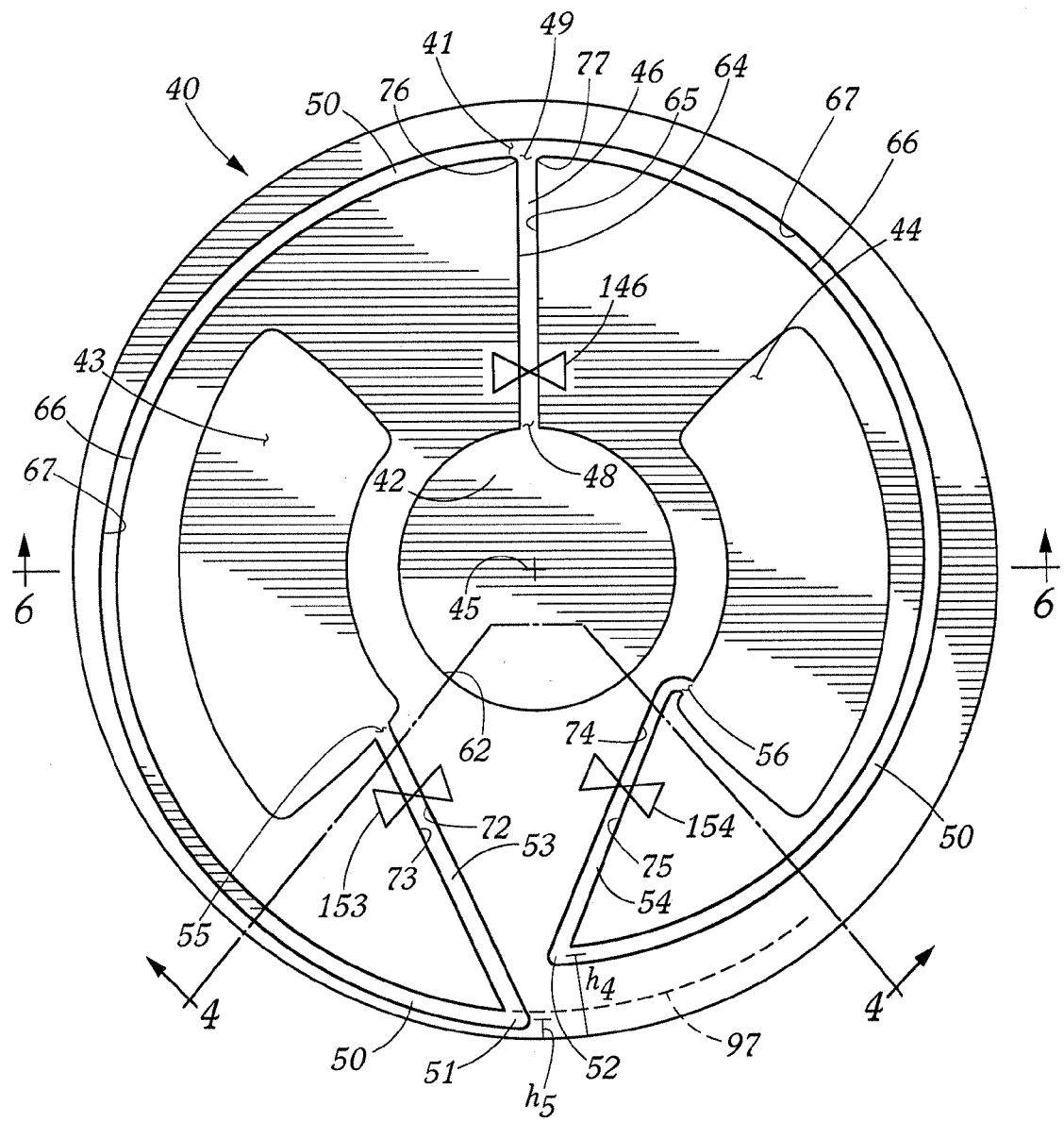
FIG. 3 is a plan view of a rotor as shown in FIGS. 1 and 2.
Figure 4:
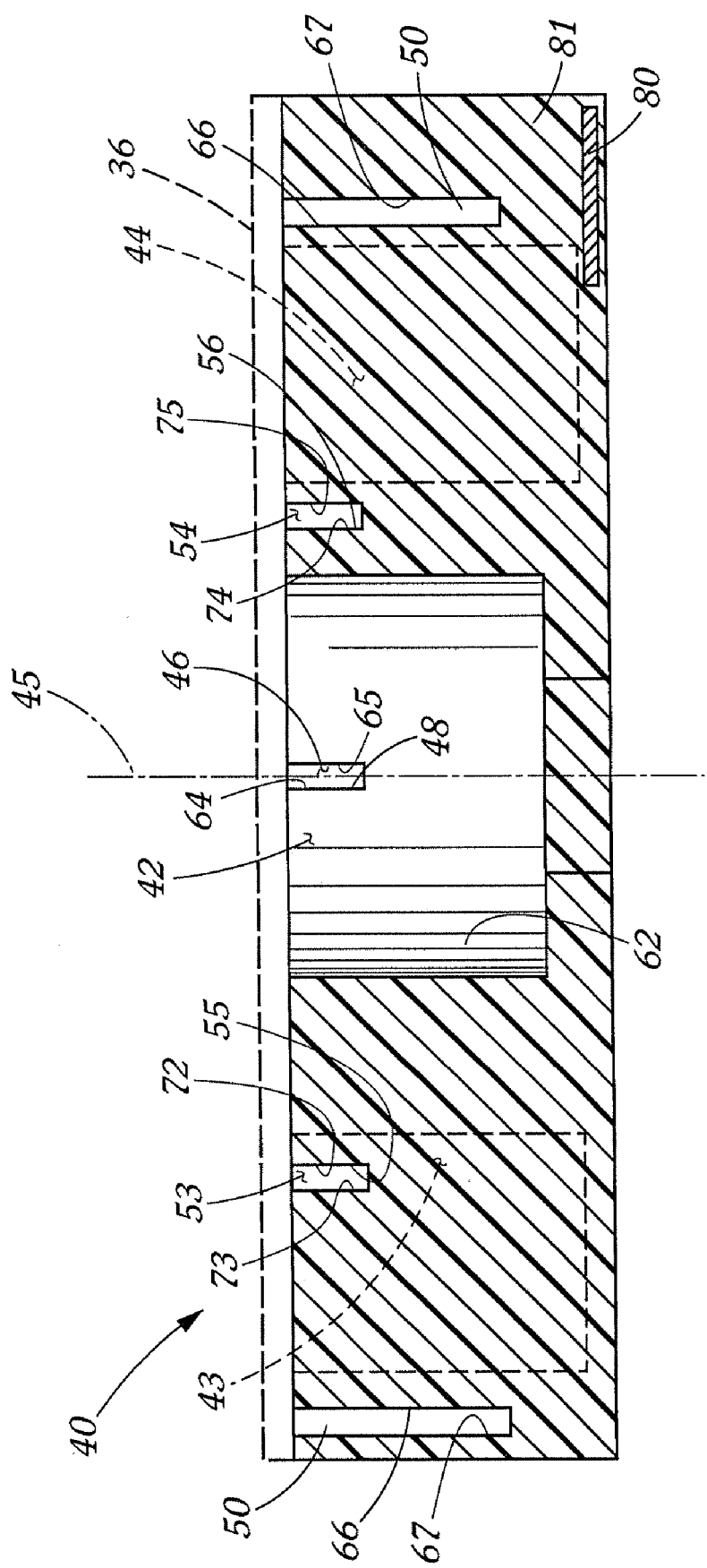
FIG. 4 is a cross-sectional view of the rotor of FIG. 3 taken along line 4—4, thereof.

As shown in FIG. 1 and also as shown in FIGS. 2 and 3, a preferred rotor 40 has four general areas; namely, a separation area 41 where the separation is accomplished, a whole blood containment area 42, an RBC (red blood cell) area 43 where RBCs are collected preferably in a storage container (see below), and a plasma area 44 for collection of plasma. The separation portion or area 41 of a preferred internal rotor 40 of centrifuge unit 14 is shown in more detail in FIGS. 2 and 3 (and see FIGS. 7 and 8, described below). In this embodiment (see FIG. 2), the separation portion 41 may also be referred to as including or being part or all of a substantially peripheral separation channel 50 of the rotor 40. As depicted here, the separation portion 41 is a feature of an overall fluid flow configuration presented by rotor 40 which preferably provides a fluid pressure drive relationship for forward flow control and a pressure balance relationship for component interface control. Thus, the rotor configuration includes a substantially central composite fluid containment pocket or area 42 which is connected in fluid communication with a radial transport channel 46 via a radial inlet port 48 defined therebetween. Radial transport channel 46 runs preferably radially outwardly to a substantially circumferential separation channel 50 which branches at the inlet 49 thereto. The adjective circumferential is intended here to indicate the channel which is at or near the circumference of the rotor 40, and traverses a path which is somewhat circumferential there around with exceptions as described below. Transport channel 46 (also referred to as an inlet channel 46) is open to and provides for fluid communication with the circumferential separation channel 50. Circumferential channel 50 then runs from this fluid communicative intersection at inlet 49 with the radial transport channel 46, substantially circumferentially around the periphery of rotor 40 to the respective outlet regions 51, 52 of channel 50. The outlet regions 51, 52 will be described in further detail below; however, it should first be noted that the circumferential channel 50 also provides for fluid communication herewith, and thus provides respective communication with both of the two separate outlet channels 53, 54 defined here as leading from the respective outlet regions 51, 52 to the respective RBC and plasma collection pockets or areas 43, 44. Outlet channel 53 thus connects through an outlet aperture 55 to RBC collection area 43. And, channel 54 similarly connects through an outlet aperture 56 to plasma collection area 44. Further, the cross-sectional view of FIG. 4 shows the radial transport channel 46 as it leads from the composite fluid containment area 42 to the circumferential channel 50. This FIG. 4 also shows a cross-sectional view of the first outlet channel 53 leading inwardly from the circumferential channel 50 to the first outlet aperture 55, and also shows a cross-sectional view of the second outlet channel 54 as it leads also inwardly to the second outlet aperture 56.

Note channel 50 has a preferred spiraled shape such that the heavier separated component outlet area (here area 51) is located radially further outwardly than the lighter phase outlet area (52, here). Separation and flow mechanics which follow from this configuration will be described in further detail below.

As depicted primarily in FIGS. 1–3, as well as in the cross-section of FIG. 4, the respective whole blood/composite fluid containment area 42 and channels 46, 50, 53 and 54 are preferably defined by substantially vertical walls, such as the peripheral wall 62 which defines the containment area 42, the radial walls 64, 65 which define the radial transport channel 46, the respective inner and outer, substantially circumferential walls 66, 67 defining the circumferential channel 50, first outlet channel walls 72, 73 defining the first outlet channel 53 and the second outlet channel walls 74, 75 which define the second outlet channel 54. Generally, adjacent walls are preferably coterminous with each other and may thus meet at corner edges, or transition zones such as the corner edges or zones 76, 77 disposed between respective adjacent walls 64 and 66; and 65 and 66 at the intersection 49 of radial channel 46 with circumferential channel 50. Though some edges are shown, adjacent walls may, however, more preferably merely blend into each other or meet in a graduated merging fashion such as may be understood from these rounded edges 76, 77 at the meeting of inner circumferential wall 66 with the inlet channel walls 64, 65 as they lead into and eventually define the inlet/intersection area 49 (see FIGS. 2 and 3).

Overhanging lips or ledges 60 and 70 (not shown in FIGS. 1–4; but see FIGS. 6A, 6B and 6C, described below) may also be preferably disposed in and around the inlet fluid containment area 42 (see ledge 60 in FIGS. 6A, 6B, and 6C) and/or around external walls of collection areas 43, 44 (see ledge 70 in FIG. 6C) to retain fluids within areas 42, 43 and/or 44, as will be described further below. Though not shown here, overhanging lips of this sort may also be disposed on or over other walls covering other fluid passageways or channels such as the circumferential channel 50, e.g. as may be desired. Further descriptions of such alternatives will become more apparent below. As another alternative, a covering ceiling may be provided by lid 36 (shown open in FIG. 1 and in dashed lines over rotor 40 in FIG. 4) which can be attached over the respective areas 42, and/or 43, 44, and/or channels 46, 50, 53 and 54 to retain the fluids therein. Other examples of such ceilings are shown and described with respect to the alternative embodiments of FIGS. 9, 10 and 11A–11D, see below.

Also note in FIG. 4 a piece of metallic material 80 is preferably disposed within the lower part 81 of the rotor 40. At least one such piece of metallic material 80 is preferably disposed therein to interact with the preferred magnetic drive force of the rotating magnetic field generated by the base 12 to spin the rotor 40 about the rotational axis 45 (see description below) preferably within a substantially stationary housing 30.

Note, the rotor 40 shown in FIGS. 1–4 may be formed by various methods using a variety of materials. However, molded plastic may provide one simply recognizable form. Lightweight yet durable parts are preferred. Simply designed pockets 42, 43, 44 and channels 46, 50, 53 and 54 may then be easily constructed in a weight balanced rotor 40 particularly relative to the semi-spiraled channel 50; where outlet 51 is disposed further radially outward than outlet 52. The rotor 40 may also be made for disposability (as for example, if the rotor 40 may be used for blood separation without a bag set 16, see, e.g., a fluid tight lid 36 as disposed on rotor 40 in FIG. 4 which could thus be used for such a purpose); or, more likely, may be made for numerous repetitive uses with a series of discrete bag sets 16; such bag sets providing for complete sealed enclosure of the blood and blood components therein so that the rotor 40 does not come into contact therewith. Rotor 40 would then require limited or no sterilization or disposal after each use.

Figure 5:
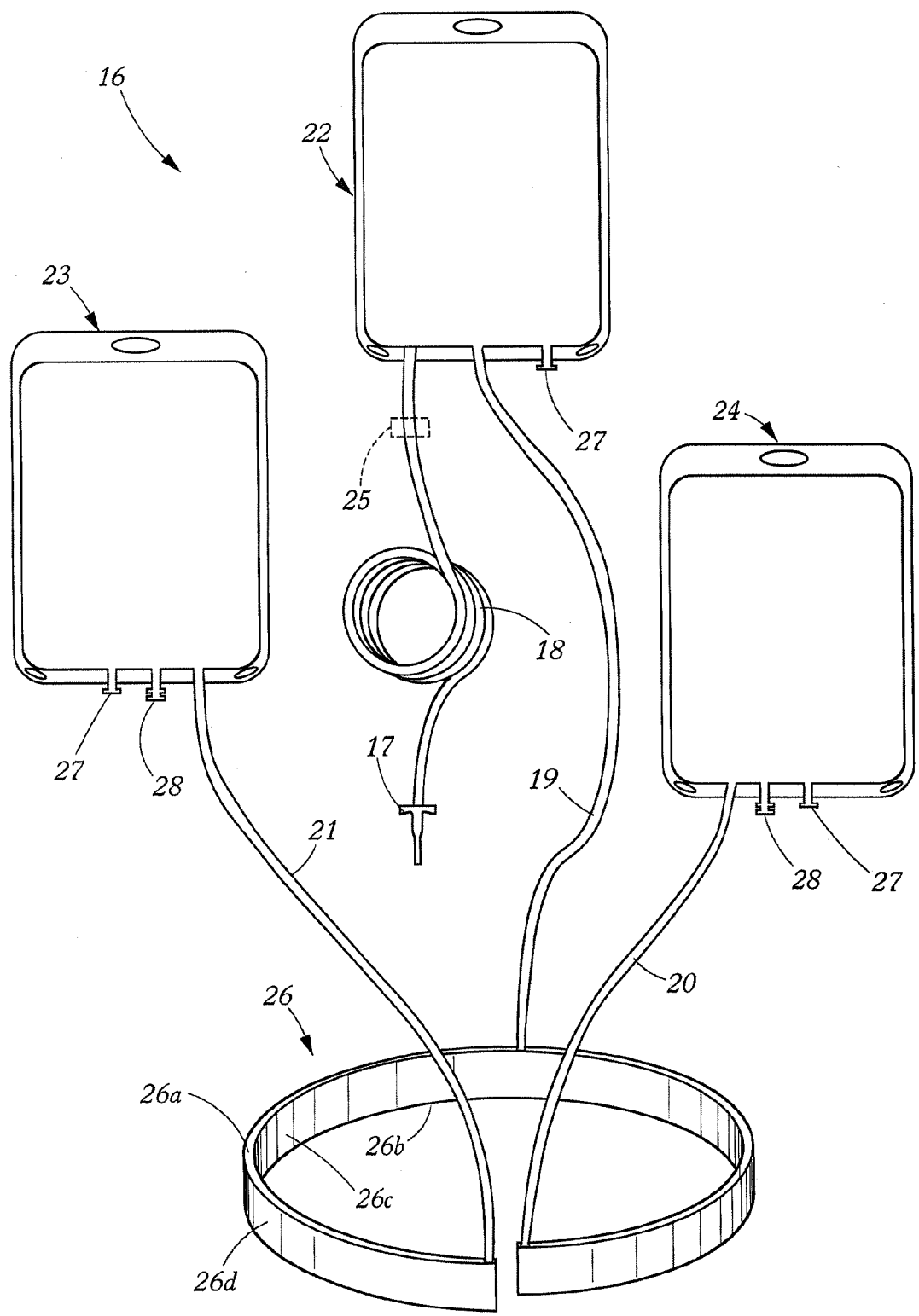
FIG. 5 is a view of a tubing and bag system as in the embodiment of FIG. 1.

As introduced in FIG. 1 above, the preferred system 10 uses a tubing and bag system 16 which is shown in more detail in FIG. 5. As shown here, this bag system 16 includes three bags 22, 23 and 24 each connected to a centrifugal separation vessel 26 through respective tubing lines 19, 20 and 21. A fourth tubing line 18 is, as shown, connected to a needle/access device 17 which can be used to connect the system 16, and particularly bag 22 to a donor/patient 11 as in FIG. 1. After an initial collection, the majority portion of tubing line 18, together with needle/access device 17 may be sealed off from and cut and/or removed from bag 22 using, in one example, a radio frequency (RF) heat sealing device (not shown) as understood. This removal may be made at a portion of tubing line 18 near bag 22 as indicated by the dashed line box 25, e.g. See also, FIGS. 6A, 11B and 16, which show the sealed end 25a of tubing line 18 after such a disconnection. As will be described, similar disconnections of bags 23 and 24 (and perhaps also of bag 22 from vessel 26) at their respective tubing lines is also preferable, though occurring after the centrifugal separation process. In a preferred embodiment, each of the bags 22, 23, and 24 also includes an air vent structure 27 to either allow air to enter the bag (as it could in bag 22 as whole blood leaves the same during use) or allow air to leave the bag (as it might in bags 23 and/or 24 when respective separated components would flow thereinto during centrifugation, see description below). Microbiological filters (0.2 micron size and the like) may be used in vents 27 to maintain sterility. Further, each of the bags may also include a port structure 28 (see bags 23 and 24 in FIG. 5; but not shown for bag 22 therein) for, among others, subsequent access to the collected separated components which may be disposed therein. Other structures and/or uses therefor may be disposed on or in or for each bag as may be understood and/or desired in the art (see, e.g., frangible closures as in FIG. 16, below).

Note, construction of the bag and tubing line parts of system 16 may take many understood forms and use many known materials. Flexible materials are preferred. For example, RF or heat welded sheet plastic (e.g. plasticized PVC bags and extruded flexible tubing lines are preferred (though blow-molded or other types of containers (e.g., glass) and lines may be used). Even vessel 26 may be formed from RF or heat welded flexible plastic sheets in an elongated form (see generally FIG. 16, also). However, vessel 26 may be molded (or otherwise formed) into a somewhat rigid device if desired, and/or may include discrete parts such as a top 26a and bottom 26b, an inner wall 26c and an outer wall 26d. On the other hand, vessel 26 may be an integrally formed unit (molded, extruded or otherwise) without discretely identifiable parts. For example, vessel 26 may even simply be a tubing line much like the other tubing lines, though perhaps of a larger inner diameter. Vessel 26 may also be very flexible and take its shape primarily from channel 50 in which it is disposed during use. Or, vessel 26 may be moderately flexible, having a particular shape retention or resilience, yet being pliable before, during or after use. Vessel 26 may also be a substantially rigid part, formed into the preferred operable shape for centrifugation and separation of the component elements therein.

Returning now to FIGS. 1–3 and including some reference to FIGS. 5, 6A, 6B and 6C, a general description of the preferred blood and blood component flow paths, when device 10 is used for the separation of blood into components, will now be described. First, note that the flow paths are preferably within bag and tubing set 16 as disposed within rotor 40 (see FIGS. 1 and however, in some embodiments, a bag set may not be used and the respective flows may simply be in the channels and pockets of rotor 40. In any case, as generally shown, particularly in FIGS. 1 and 5, for the tubing line flow paths, whole blood is drawn from the donor 11 and flows through needle 17 and tubing line 18 to the bag 22 perhaps while bag 22 is in, but preferably before disposition of bag 22 in the centrifuge device 14. If before disposition in rotor 40, then bag 22 may be disposed in a separate container (not shown) or hung from a hook (not shown) as understood in the art for collection of whole blood from a donor 11. If as shown in FIG. 1, and as preferred, no pump is used along line 18, then tubing line 18 will be connected to the bag 22 in a fashion which preferably allows for gravity drainage thereinto. A temporary outflow stopper as by a frangible connection or a slide or roller clamp (not shown in FIG. 5) may be used in line 19 during collection in bag 22. Briefly, also shown in the FIGS. 1 and 5 depictions, are the other tubing lines 19, 20 and 21 of tubing system 16 which provide the inlet and exit flows to and from the vessel 26 as this will be disposed in the centrifuge rotor 40 during subsequent centrifugation. Thus, during such centrifugation (and preferably after disconnection from donor 11 and after cutting away tubing 18 and needle 17 at cut off point 25 as described above), the whole blood will be made or allowed to flow from bag 22 to the vessel 26 through tubing line 19, and after separation in vessel 26, the separated blood components; namely, red blood cells (RBCs) and plasma will flow through respective tubing lines 21, 20 for collection in respective containers 23, 24; RBCs in line 21 to container 23 and plasma through tubing line 20 for collection in container 24.

Note, shown schematically also in FIG. 3 are optional clamps or valves 153 and 154 disposed in or adjacent channels 53, 54 and which may be used to ensure no flow conditions in channels 53, 54 until desired, as for example, until a sufficient rotational speed has been achieved. These may thus be centrifugal clamps which may be disposed on the rotor 40 and may be automatically activated by the achievement of a particular minimum rotational speed of rotor 40. Alternatively, these clamps may be manual (typical pre-rotation activation) or automated by other mechanical and/or electrical means to open and/or close during (or before or after) rotation. A similar optional valve 146 may also be disposed on inlet channel 46 as shown in FIG. 3 as well.

Figure 6A:
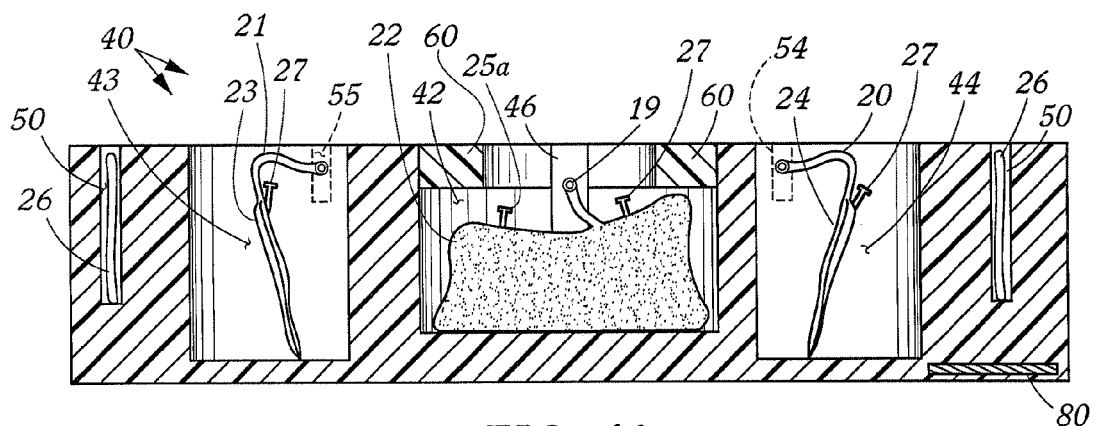
FIGS. 6A, 6B and 6C are cross-sectional views of the rotor of FIG. 3 taken along line 6—6 thereof and including a tubing and bag system as in FIG. 5 therein.
Figure 6B:
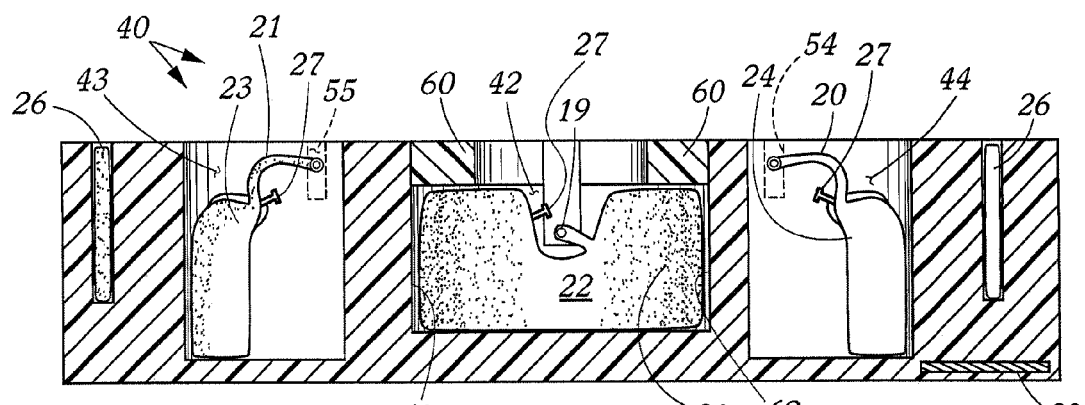
Figure 6C:
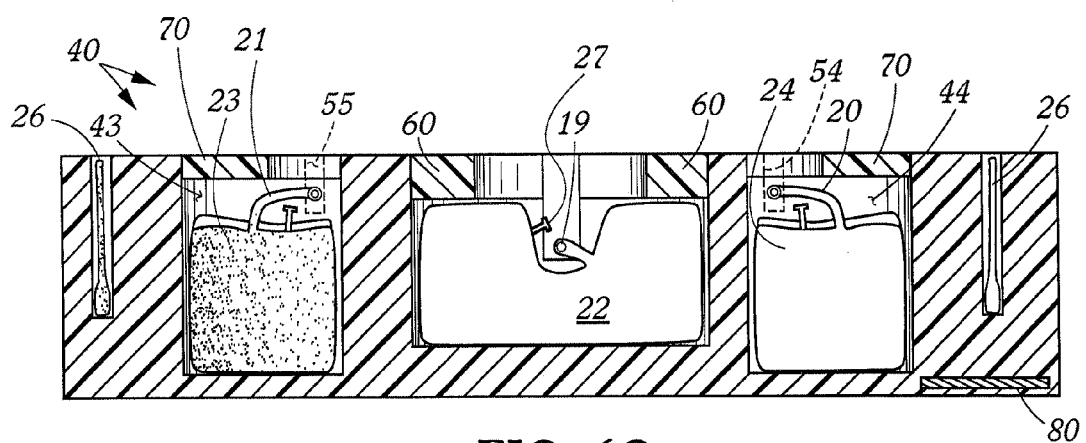

Prior to and during centrifugation, tubing lines 19, 20 and 21 are preferably disposed in corresponding channels formed in the rotor 40. Thus, the flows in and through the centrifuge unit 14 of the separation device 10 are as follows (with or without tubing lines, as introduced above). Whole blood from the donor 11 now preferably contained in bag 22 (or perhaps collected otherwise, e.g., directly into rotor 40) is initially placed in the composite fluid containment area 42 of the rotor 40. The empty collection bags 23, 24 are preferably positioned in their respective collection pockets 43, 44 as are the respective tubing lines 19, 20 and 21 within their respective channels 46, 53, 54. Vessel 26 is likewise preferably disposed in the channel 50. See FIG. 6A. While in the receiving/contain area 42, the blood is then exposed to centrifugal forces when rotor 40 is spinning (which the rotor 40 is preferably made to do after the whole blood (preferably in bag 22) is placed into or is otherwise resident within centrifuge unit 14). Note, the initial exposure of blood to the centrifugal forces is relative to the axis of rotation 45 (see FIG. 3 where axis 45 is shown as a crosshead indicating the perpendicularity thereof relative to the drawing sheet and see FIG. 4 where it is shown as a dot-dash line). Under the centrifugal forces of the spinning rotor 40, the blood is moved to the periphery of the containment area 42 (see FIG. 6B) and is thus generally moved into a generally abutting relationship with the wall 62 which defines the containment area 42. As can then be seen from FIG. 6B the whole blood (identified generally therein by the reference number 90) is preferably held substantially vertically within the receiving area 42 by either an overhanging lip 60 (as shown in FIGS. 6A, 6B and 6C) or a lid 36 (as shown in dashed lines in FIG. 4). The blood 90 may also take on a quasi-parabolic shape under such a lip 60 such as is shown in FIG. 6B when subjected to the centrifugal forces of a spinning rotor 40. Note, in a preferred embodiment, air may be allowed to flow into bag 22 as whole blood first seeks the outer wall 62 of the containment area 42, and still further during operation as whole blood leaves the containment area 42. Though not necessary, air may also be allowed to leave bags 23, 24 as separated components enter. Such air ingress and egress may preferably pass through respective vents 27 (FIGS. 5 and 6A and 68). Microbiological filters (e.g. 0.2 microns) may be used in vents 27 to maintain sterility inside the closed bag system 16.

A continuous flow of the whole blood 90 will then escape from the fluid receiving area 42 into the radial channel 46 through tubing line 19. This blood will then travel radially outwardly and then flow into the circumferential channel 50. This is shown schematically in FIG. 7 wherein flow arrows are provided to show the direction of flow throughout the preferred centrifugation configuration therein. This first radial flow is indicated by flow arrow 85 and then continues on, into and goes both ways (see arrows 87 and 88) around the circumferential channel 50 for ultimate passage out of the separation area 41 through the outlets 51, 52, channels 53, 54 and apertures 55 and 56 (see FIGS. 2 and 3). First, it should be noted that when the centrifuge rotor 40 is spinning (again, as it preferably will be whenever blood is disposed therein), this will impart centrifugal forces on the blood which will then separate it into two primary components; namely, red blood cells (RBCs) and plasma. The heavier RBCs will settle outwardly under these centrifugal forces, and will thus accumulate, in a still continuously circumferentially flowing fashion, against or adjacent outer wall 67 of channel 50. This action is shown in detail in FIG. 7, wherein both the radial and the circumferential flows are indicated with arrowheads in the respective channels 46, and 50. The RBCs are identified generally by the reference number 91 in FIG. 7, and the plasma is similarly identified generally by the reference number 92. Also, it should be noted that component separation will likely generally occur, as shown partially in FIG. 7, throughout the travel of the blood around the circumference of the separation area 41 within the circumferential channel 50. For this reason, the circumferential channel 50 may also be referred to as the separation channel.

Figure 7:
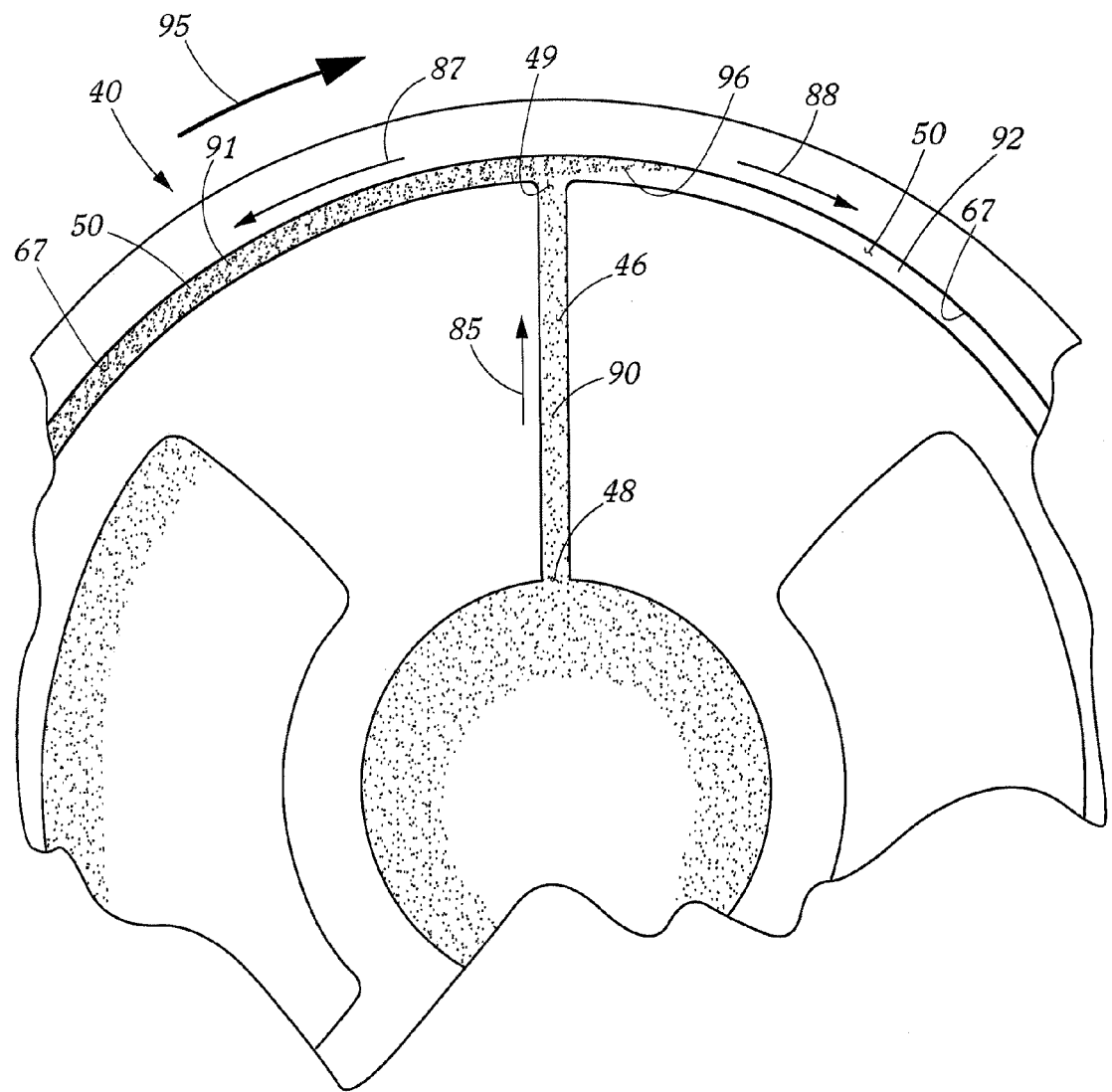
FIG. 7 is a broken away, plan view of a portion of the rotor of FIGS. 1, 2 and 3.

Moreover, although a generally counterclockwise flow pattern as depicted by the arrowhead 87 for RBCs within the channel 50 is shown with a clockwise centrifugal rotation 95 of rotor 40 as shown in FIG. 7, this is not intended to be limiting as centrifugal rotation 95 may be counter-clockwise, or clockwise RBC flows are also foreseeably operable with a clockwise or a counter-clockwise rotor rotation 95. Similarly depicted is a clockwise plasma flow 88 with a clockwise rotation of the rotor 40 as indicated by the large arrow 95 in FIG. 7, although again, opposite directions and/or combinations of directions for any of these flows are foreseeable as well.

Even though the flow in and through the circumferential channel 50 is where a substantial part of the separation takes place such that the RBCs are forced toward the outside wall 67 (see FIG. 7), the fluid flow (as well as the fluid separation) is nevertheless preferably continuous throughout. In other words, the inlet flow of whole blood to channel 50 is preferably continuous as are the outlet flows of plasma and RBCs from channel 50. This flow continuity is preferably driven by the relative off-set "heights" of the inlet and outlet ports 48, 55 and 56 as will now be described in more detail. The term "heights" is used here in a fluid dynamic, fluid pressure-balance sense for referring to various fluid distances measured from a common baseline such as the outer rotor or fluid flow circumference or a similar circular reference (see exterior rotor surface 97) of the centrifuge separation area 41 radially inwardly toward the axial center 45, See, e.g. FIG. 8 which has generally wider channel portions to assist in demonstrating the respective "heights." More specifically, the height of the radial transport inlet port 48 of channel 46 is the height, or radial length of the radial channel 46, also designated as $h_1$ in FIG. 8 from the reference circle 97 to the inlet port 48. Note, rotor reference circle 97 is thought to be substantially arbitrary in its position (i.e., no specific radius required), the primary conception of which is that it provide a substantially common baseline from which to measure the relative heights, $h_1$, $h_2$, and $h_3$. Even so, one preferred datum or reference (of various possible) is in the fluid flow channel as for example at the heavy phase/red blood cell outlet (generally referred to as outlet 51) from the peripheral channel 50; see dashed line reference circle 97 in FIG. 8.

Figure 8:
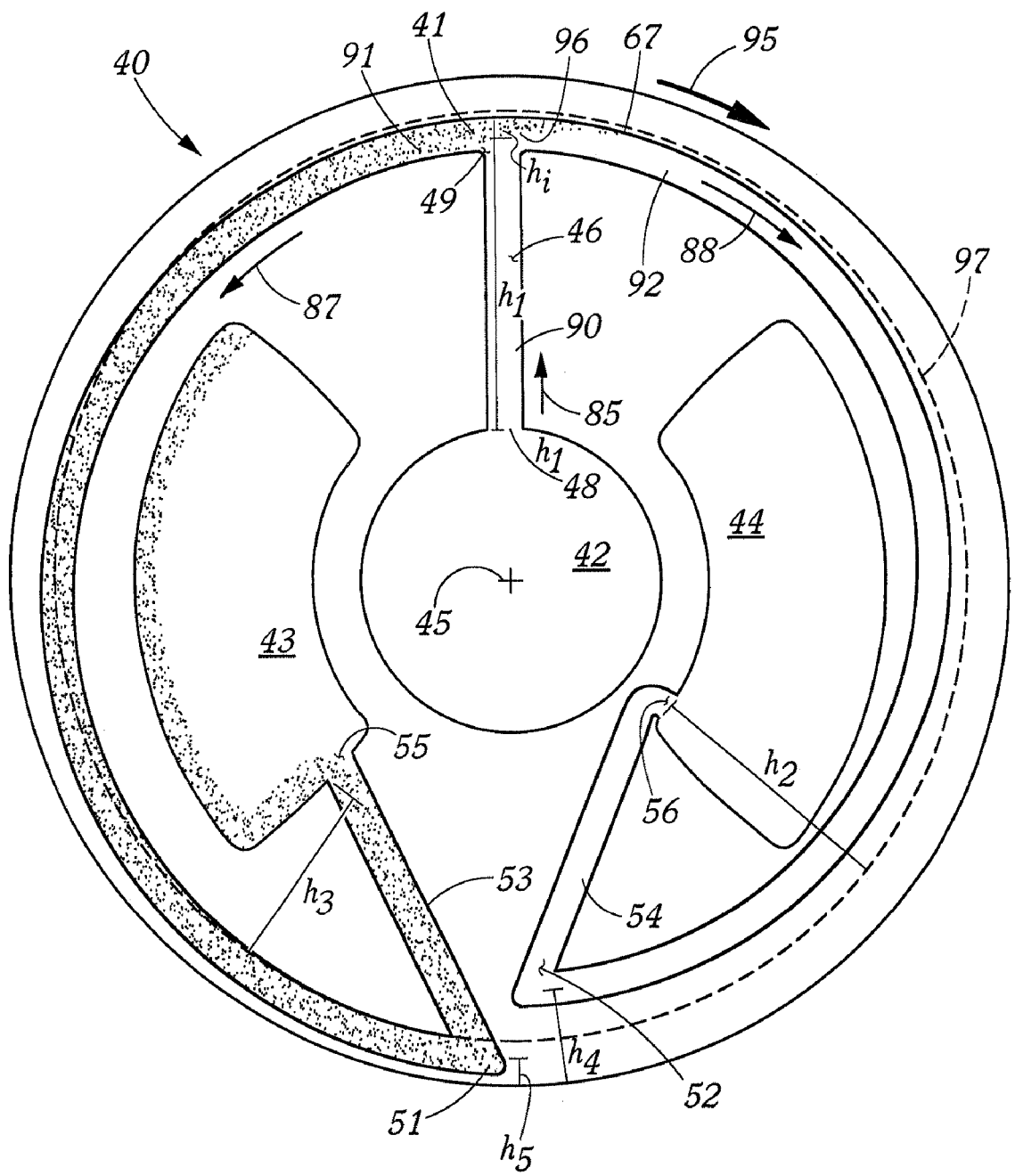
FIG. 8 is an alternative plan view of a rotor such as that shown in FIGS. 1–4 shown in use.

Then, as the inlet port height is the relative height of the inlet flow channel 46, and is designated $h_1$; so also are the outlet port heights the relative heights of the outlet flow channels 53,54 to the outlet ports 55, and are designated $h_2$ and $h_3$, respectively in the same FIG. 8. Then, for a fluid to be able and/or driven to flow from the inlet 48 toward the outlets 55, 56, the inlet fluid static pressure, $\rho_1 g_1 h_1$, in the inlet transport channel 46 must be greater than either or each of the two outlet fluid static pressures, $\rho_2 g_2 h_2$ and $\rho_3 g_3 h_3$ ($\rho_{(1,\ 2\ or\ 3)}$ is the fluid density, $g_{(1,23)}$ is the gravitational or centrifugal acceleration quantity and $h_{(1,\ 2}$ is the relative fluid height of each channel inlet or outlet port as described above). Thus, for the preferred positive flow in the direction of the arrows in FIGS. 7 and 8;

$$\rho_1 g_1 h_1 > \rho_2 g_2 h_2, \text{ or, } \rho_1 g_1 h_1 > \rho_3 g_3 h_3 \quad \text{(Equation 1)}.$$

Furthermore, though accurate as a generalized concept, this summarization is both subject to simplification and/or may in other ways be somewhat over-simplified. The primary invention selectable driving values are the respective h quantities as have been distinctly defined above. However, even though the respective g gravitational or centrifugal acceleration values are more purely non-constant variables (as depicted by the subscripts 1, 2 and 3 therein), particularly in view of the large centrifugal forces applied in the present system and the different radial lengths of each column, these may be nevertheless considered substantially similar values, at least in considering which respective values will be more responsible for driving the entire equation. Moreover, particularly when considering the driving variable relationships herein under practical consequences (the h's and ρ's will vary more widely than the g values); the g values may be considered as substantially equivalent values throughout the above equation for each of the above fluid pressure terms (at least when operating within a substantially common centrifugal force field and RPMs). In other words, the differences between the different g values are small enough such that the selection of the respective h values will more than accommodate for the differences therein in the desired centrifugation configuration. Similarly, though the ρ values will likely provide greater distinctive differences for each term in this formula than the g values, the relative h values may be chosen in design to accommodate for these also. Note also however, these ρ values are dependent on the fluids flowing herein and are not as amenable for selecting or for establishing the desired configuration. In blood separation, the first ρ value, in $\rho_1 g_1 h_1$, is the density of the composite fluid in the transport channel 46; here in the principal embodiment, the density of whole blood before separation, whereas, the second and third ρ values, appearing in $\rho_2 g_2 h_2$ and $\rho_3 g_3 h_3$, represent the respective densities of the fluids in the two outlet channels 53, 54; here of the separated blood components, RBCs and plasma.

Moreover, the fluid pressure terms ρgh may be more accurately be considered as summations (e.g., $\Sigma(\rho gh)_n$) of contributing parts whether of unit parts of the length (e.g., where the density of a constant fluid may exhibit variation along the length or height of a column; summation or even integration may be used herewith) or when perhaps multiple fluids more accurately contribute to the pressure in a given column. As a first example, the first ρ value, in $\rho_1 g_1 h_1$, includes both a whole blood and an RBC component, such that the pressure term $\rho_1 g_1 h_1$, is actually the sum ($\Sigma(\rho gh)_1$) of an $\rho_{RBC} g_{RBC} h_i$ value and an $\rho_{whole\ blood} g_{whole\ blood}(h_1-h_i)$ value. The $h_i$ value is shown in FIG. 8 as the height of the interface of the separated RBCs 91 with respect to the separated plasma 92 in, adjacent or near the intersection 49 of the inlet channel 46 with the peripheral channel 50. The interface between the RBCs and plasma is identified by the general reference number 96 in FIGS. 7 and 8. Thus, the hydraulic pressure term for the inlet channel 46 is the sum of the above interface related values as in $$\rho_1 g_1 h_1 = \rho_{RBC} g_{RBC} h_i + \rho_{whole\ blood} g_{whole\ blood}(h_1-h_i).$$

The terms for use in the selection of the respective heights for creating the preferred positive direction flow according to Equation 1 are thus more fully defined. For example, Equation 1 can approach: $\Sigma(\rho gh)_1 > \Sigma(\rho gh)_2$, or, $\Sigma(\rho gh)_1 > \Sigma(\rho gh)_3$ Similarly, the second $\rho$ value, in $\rho_2 g_2 h_2$, includes at least a plasma and usually also an RBC component, such that the pressure term $\rho_2 g_2 h_2$ is actually the sum $(\Sigma(\rho gh)_2)$ of an $\rho_{RBC} g_{RBC} h_i$ value and an $\rho_{plasma} g_{plasma} (h_2 - h_i)$ value. Thus, the hydraulic pressure term for the outlet channel 54 is the sum of the above interface related values as in $$\rho_2 g_2 h_2 = \rho_{RBC} g_{RBC} h_i + \rho_{plasma} g_{plasma}(h_2 - h_i).$$

Still further, it is the location of the interface 96 between the RBCs and the plasma which is, according to the present invention, sought to be controlled such that the height, $h_i$, thereof remains within a certain preferred range as the interface 96 meets with respective walls 66, 67 of the circumferential channel 50. This height, $h_i$, of interface 96 will thus preferably be so maintained by the pre-selection of the respective heights $h_2$ and $h_3$ so that they are related to each other such that the fluid pressure values of $\rho_2 g_2 h_2$ and $\rho_3 g_3 h_3$ (as generally introduced in Equation 1, above) are equal to each other, i.e.;

$$\rho_2 g_2 h_2 = \rho_3 g_3 h_3 \qquad \text{(Equation 2)}.$$

This then provides a hydraulic or hydrostatic pressure balance to maintain the interface at a substantially static height, notwithstanding the continuous inflow into and outflow from channel 50. But note here also, the $\rho$ value in this $\rho_3 g_3 h_3$ may have both an RBC and a plasma component such that $\rho_2 g_2 h_2$ is again the sum of a $\rho_{RBC} g_{RBC} h_i$ and a $\rho_{plasma} g_{plasma}(h_2 - h_i)$ ($h_i$ again being the height of the interface, as shown in FIGS. 7 and 8). And, Equation 2 can become more particularly;

$$\rho_2 g_2 h_2 = \rho_{RBC} g_{RBC} h_i + \rho_{plasma} g_{plasma}(h_2 - h_i) = \rho_3 g_3 h_3 \qquad \text{(Equation 3)}.$$

Note, the $\rho_3 g_3 h_3$ pressure term here could also be thought of in composite parts; however, as shown and described it will generally have only one component fluid (the heavier phase separated component) and thus may be thought of more generally (for example using an average g value and an average $\rho$ value to arrive at a single $\rho g$ value such as $\rho_{RBC} g_{RBC}$ for separated RBCs.

Note, in the preferred situation where $\rho_1 g_1 h_1 > \rho_2 g_2 h_2$ or $\rho_3 g_3 h_3$ and where $\rho_2 g_2 h_2 = \rho_3 g_3 h_3$, the flow dynamics here will be such that in any event where any part of any term changes, the selected relationship will bring the pressure terms as a whole back or automatically readjust to equalization. Thus, if for some reason $\rho_3$ were to change (e.g., become lesser or greater) during operation, then flows will change such that the interface $h_i$ will move to counteract this change. In an example if the $\rho_3$ were to become greater such that the $\rho_2 g_2 h_2$ term would tend to grow in value, then the $\rho_3 g_3 h_3$ term would tend to grow, likely by flowing faster (or likely at least not at its previous rate) and gain by raising the interface, e.g., the $h_i$ term in the previously established relationship:

$$\rho_2 g_2 h_2 = \rho_{RBC} g_{RBC} h_i + \rho_{plasma} g_{plasma}(h_2 - h_i)$$

As another example, if the less dense component (e.g., plasma) lessens at any time, it will get preferential flow out of one port (e.g., the plasma port), and the heavier component (e.g., RBCs) will slow or not flow until the $\rho_2 g_2 h_2$ term increases as described above, e.g., when the $h_i$ term rises sufficiently. Moreover, all three columns will go toward equalization in a no-flow situation (e.g., the $h_1$ will drop to a level (particularly if no further fluid supplies the inlet channel 46) such $\rho_1 g_1 h_1 = \rho_2 g_2 h_2 = \rho_3 g_3 h_3$; at which point flow will be stopped. This provides an automatic flow stop or shutoff feature when supply of composite fluid in containment area 42 is extinguished (the heights will then generally assume a relationship such as $h_2 > h_1 > h_3$). In any event, these relationships will tend to drive toward an equalization, even if flow in one or more of the columns stops for a period; and the terms may not always be equal, but they will equalize.

In all of these cases then, the configuration selectable values are preferably the h values. The particular fluids to be and consequently are separated dictate the $\rho$ values, and the g values are governed mainly by the materials involved and the centrifugal forces applied to the system. Thus, when deciding the size and relative configuration of the desired centrifugation system, the selectable values are the inlet channel height or length $h_1$ relative to outlet channel heights $h_2$ and $h_3$; as well as the relative outlet heights $h_2$ and $h_3$ to each other according to the above Equations 1 and 2 and 3. Note, it is also preferable to choose relative channel outlet heights $h_4$ and $h_5$ such that the plasma outlet 52 represented by height $h_4$ in FIG. 8 is radially further inward than height $h_5$ which represents the RBC outlet 51 from channel 50. Moreover, it is further preferred that $h_4$ and $h_5$ are related to $h_i$ (even though shown relative to two different reference circles) such that $h_i$ is disposed above $h_5$ and below $h_4$ to assist in maintaining the interface within the channel 50. This constitutes a preferred definition of a semi-spiraled configuration of channel 50 relative to the rotational axis 45 (see FIG. 8).

Control over interface 96 using Equations 2 and 3 provides a distinct advantage. First, if interface 96 were not so controlled, it could fall either radially outwardly along wall 67 so that separated plasma could ultimately spill into the RBC outlet channel 53 and undesirably dilute the RBC product flowing through outlet 55 to collection area 43. Or, the interface 96 could alternatively, ride too high, radially inwardly, along wall 66 such that a buffy coat component and/or RBCs could spill into the plasma outlet 56 into plasma collection area 44. The "buffy coat" blood component, as known in the art, generally rides on the interface 96. The buffy coat generally includes platelets and white blood cells therein. And, if the interface 96 is not controlled or maintained a sufficient distance from either of the outlets 55, 56, then these buffy coat blood components could spill into and contaminate either of the RBC or plasma products. White blood cells (WBCs) are particularly unwanted in both RBC and plasma products due to the possible contamination of such white blood cells with certain undesirable pathogens, including HIV viral contamination, for example. However, because centrifugal separation will less effectively separate WBCs from RBCs, the WBCs are more likely to be addressed separately relative to the RBCs with a (pre- or) post-centrifugal filtration. In other words, the present invention, like other centrifugal separation systems, will likely not sufficiently leukoreduce red blood cells. Rather, although the buffy coat including the WBCs will preferably ride on the RBC layer, they will not likely be sufficiently separated from the RBCs here so as to produce a leukoreduced RBC product. However, the buffy coat including WBCs can be sufficiently centrifugally separated from the plasma product by the present invention so long as the height of the interface $h_i$ is sufficiently controlled as taught herein. Note, the buffy coat may be retained sufficiently in vessel 26 (particularly using the automatic shutoff feature described above) so that the buffy coat may be collected and further processed into component parts (such as platelets, e.g.) for further use in transfusion, e.g.

Nonetheless, once the whole blood 90 has traveled through the separation channel 50 and has been separated into components, particularly into RBCs 91 and plasma 92, then these components 91 and 92 will flow out through their respective outlets, namely outlets 55 and 56 into collection areas 43, 44. Again, even though this is generally a batch process, the flow during separation is a continuous flow process such that during the process the whole blood 90 continuously flows into the centrifugal configuration, particularly the separation portion 41 of the channel 50 of the centrifuge rotor 40, and blood components 91 and 92 are continuously separated therein and continuously flow out of the centrifugal configuration separation portion 41 of the centrifuge channel 50 through the outlet channels 53, 54 to and through outlets 55 and 56 into the respective collection areas 43, 44 of rotor 40.

Specifically, returning to FIGS. 6B and 6C where the above-described embodiment is shown such that flow through the respective RBC and plasma outlets 55, 56 (also known as container inlets 55, 56) and tubing lines 21, lead ultimately to fluid containers 23, 24. Note, in the embodiment shown here, the fluid is still in the centrifugal field as well as in the fluid pressure drive and balance which forces a forward flow from containment area 42 to the respective collection areas 43 and 44. This pressure drive may thus be a fluid flow pressure which forces a flow of the fluid in and through the respective RBC and plasma outlet tubing lines 21, 20, and a further flow even upwards (if necessary or desired), against the pull of gravity out of channel 50 and vessel 26 into the storage bags 23, 24.

Several important advantages are achieved with a device such as that shown and described herein. A first such advantage is the elimination of numerous control elements which were often required in previous centrifugal separation systems. For example, the hydraulic pressure-balanced interface control shown and described here eliminates the need for optical or other feedback loop interface control elements (including pumps, for example). The present pressure-balance controls can also be substantially independent of the blood hematocrit (within normal ranges of donor hematocrit) and relative flow rates of the inlet and outlet fluids. This eliminates the need for complex flow rate calculations and pumps and pump controls therefor (i.e., eliminates computer calculations and multiple flow control pumps; in various conventional embodiments, multiple pumps, inlet and outlet, have been required to be maintained in dynamic control relationship with each other constantly by computer in order to provide proper interface control). Thus, at the least, no inflow pump is required here, and blood may instead be fed from the whole blood container 22 into the separation channel 50 and vessel 26 by the centrifugal forces of the spinning rotor 40 and the fluid pressure imbalance $\rho_1 g_1 h_1 > \rho_2 g_2 h_2$ or $\rho_3 g_3 h_3$ (Equation No. 1). The lack of an inflow pump and preferred closed, but batchwise/continuous process as well as the less complex rotational drive mechanism further eliminates the need for a rotating tubing loop. This serves to greatly reduce the quantities and sizes of the mechanical components (tubing loops in rotating loop systems often generally dictate the minimum mechanical element requirements and size); and this thus also allows for an overall reduction in scale of the separation device as a whole. A closed batchwise system (no inflow pump) also eliminates any need for a rotating seal at the inlet connection of the inflow line to the separation device. This greatly reduces complexity and a large potential for operational failure. Also, the rotor and housing combination are easily made in a totally closed system which can be simply sterilized and can be completely disposable, or, as particularly in the case of rotor 40, reusable without sterilization particularly if used with completely closed, sterilized tubing bag systems 16 as described herein. The reduced scale and mechanical complexity contribute to the disposability and/or reusability benefits as well.

A further advantage can be realized in the output product quality. In particular, a virtually constant maximum hematocrit may be obtained for all resultant red blood cell products because the presently described separation device may be operated within a range of revolutions per minute (RPMs) at which the product hematocrit does not substantially vary. For example, the present invention may be operated at high RPMs; speeds which are heretofore not usually achievable for various reasons (e.g., drive mechanism or tubing loop or rotating seal problems at such high speeds). And, at such speeds, virtually all RBCs will be separated out from the input whole blood, thus yielding an RBC product with the highest available hematocrit. Note, the highest available hematocrit is a number above 80% and less than 100% and which approaches a substantially constant asymptote which is in the area of approximately 90 or 95%. At speeds in the range of high RPMs, the resulting hematocrit is virtually equivalent to the asymptotic maximum throughout that range. At much lower speeds (e.g., 3000 or below), the resulting hematocrit may significantly diverge from the asymptotic maximum. FIG. 6C shows the system at or near the end of a process such that the whole blood bag 22 is substantially empty (or filled with air) with bags 23 and 24 filled with respective RBC and plasma products and preferably little remains in the vessel 26 except perhaps preferably a usable buffy coat product.

Referring once again to FIG. 1, a few basic alternatives will now be addressed. First, it should be noted that the embodiments shown in the drawings do not immediately provide for simultaneous collection from a donor/patient or other composite fluid source 11 and centrifugal separation. Rather, the FIG. 1 embodiment is generally directed to collecting a container of composite fluid in a container 22 and then detaching from the donor 11 before starting the centrifugal separation operation. Otherwise, what is also shown as an option is the use of an anticoagulant (A/C) which may be preferred and particularly is preferred when blood is the composite fluid to be separated using device 10. In the preferred alternative, A/C may be disposed in bag 22 prior to collection such that during collection, the blood from donor 11 flows through tubing 18 into bag 22 and is then mixed with the A/C therein to form an anticoagulated blood mixture. Thus, a direct connection to a donor 11 can be made as shown in solid lines in FIG. 1. Note, the present invention may be used in a process (not shown) to separate previously collected composite fluids, like blood, without the need for anticoagulant addition (in the case of previously collected blood; such blood will very likely already have an anticoagulant added thereto by any of a variety of methods, and thus does not require additional quantities thereof). However, in another embodiment, an anticoagulant system 99 with an A/C container 99a is shown in dashed lines in FIG. 1 as it might be incorporated into the overall system. In particular, the anticoagulant container 99a may be connected to a tubing line 99b which is in turn connected to a manifold 99c disposed in fluid communication with the blood inlet line 18. Such a manifold connection is known and used frequently in this field of art. The anticoagulant may then be pumped or allowed to free flow by gravity force into the tubing line 18, such free flow being controlled by careful selection of the inside diameter of the A/C tubing line 99b.

Preferably, however, an anticoagulant pump (not shown) may be used to control the inflow of A/C into the inlet line 18. Peristaltic pumps for this purpose are well known in this field (as are other pump types; e.g., linear piston plunger pumps, among others).

Another basic alternative available with this invention involves the optional return of certain separated blood components back to the donor, rather than retaining these in the collection reservoirs 23, 24. An example embodiment for returning a quantity of either (or both) separated RBCs and/or separated plasma back to the donor 11 is not shown in the drawings but would preferably take place after the centrifugation process is completed. As such, a bag 23 containing separated RBCs and/or a bag 24 containing plasma may be removed from the rotor 40 and then treated, stored or otherwise dealt with in the ordinary course. Then, when re-infusion to the donor or transfusion to a patient is desired, an infusion line (not shown) may be connected to and through a port structure 28 in a fashion known in the art (using, e.g. a spike, needle or other sterile docking connection means). Then, when it may be desired to return a quantity of a separate component (RBCs or plasma) to the donor 11 (or transfused to another patient), the desired component may then be allowed to flow out of its respective container 23 or 24 or the like, through its respective return/infusion line (not shown), back toward and into the donor or patient 11. Accomplishment of these particular flows may simply involve gravity drainage of the desired blood component from its collection/storage bag 23 or 24, and/or it may involve the use of one or more pumps, preferably of the peristaltic type. Thus, respective pumps may be engaged with each return/infusion line (not shown) and then may be activated at a desired operational point to pump the desired separated blood component out of its reservoir and through the respective tubings, and back into the donor or patient 11.

Note, as shown and described for the most part throughout this specification, the inlet to whole blood collection bag 22 and the outlet from bag 22 as well as the inlets to bags 23 and 24 have preferably not required any pumping means, internal or external. The inlet through tubing line 18 is preferably gravity driven; and the outlet and inlet flows through tubing lines 19, 20 and 21 are preferably driven by the fluid pressure drive of Equation No. 1 and the centrifugal energy imparted to the fluid as it is subjected to the centrifugal forces imparted on the rotor 40 by the centrifuge drive 12. However, other motive means may alternatively be employed for any/either of these flows as well. For a first example, a peristaltic or other fluid pump (not shown) may be used to draw blood from the donor/patient 11 and feed the blood to the whole blood bag 22. However, it should be noted that this would preferably occur prior to centrifugation; and with (or even without) such an assist, particularly if it provides much of an increase over a gravitational pull, an additional employment of a clamping device (not shown in the drawings) on the outlet line 19 of bag 22 may be desired. An example of such a clamp could take on many of the forms known in the art.

Similarly, though centrifugal forces are preferred for moving the separated components into and out of the separation channel 50; this may be used with other motive means here as well. As a first example (not shown but introduced above) after centrifugation, the collection bags 23, 24 may be disposed lower than the separation area 41 and/or containment area 42 and the separated components may then use gravity-drainage as an assist to move the components from the separation channel 50 to the collection bags 23, 24. Another alternative involves the use of external pumps (not shown), also preferably after centrifugation, of preferably peristaltic or other alternative types to move the separated components from separation channel 50 through respective tubing lines 20, 21. Note, such pumps (not shown) may also provide greater assistance with a few of the other alternatives described above. A positive force may be desirable and/or even necessary to move remainder fluids from the channel 50 to the bags 23, 24 after completion of the centrifugation process. Thus, such optional pumps may provide a desirable assist to any centrifugal and pressure-balanced flow action; or such pumps could provide the sole driving force for drawing separated fluids from the separation channel 50, moving them through respective tubing lines 20,21 to the bags 23, 24.

Figure 9:
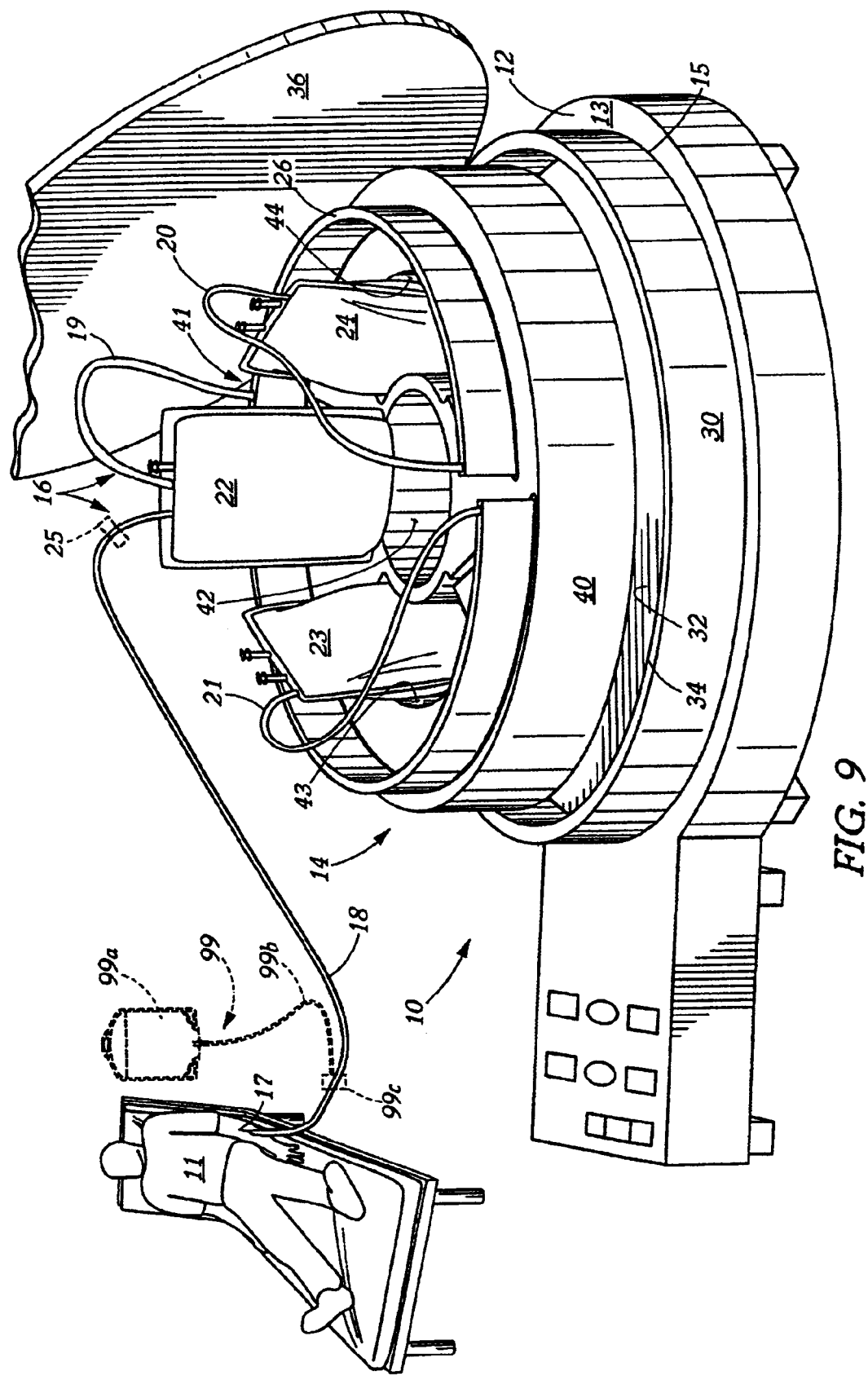
FIG. 9 is an isometric view of an alternative rotor/centrifuge of a separation system such as in FIG. 1 and like the rotor of FIG. 3.

Turning now to a few slightly more divergent alternative embodiments, reference is first made to the isometric view shown in FIG. 9. The primary distinction this centrifuge unit 14a has over that shown, for example, in FIGS. 1–4, is that the separation area 41 of the distinctive rotor 40a, as shown in FIG. 9, includes distinctive pockets serving as the collection areas 43a and 44a. The previous RBC and plasma collection areas 43, 44 (from FIGS. 1–4) have now been turned into substantially rectangular pockets 43a and 44a, in this FIG. 9 embodiment, and the pockets 43a and 44a have also preferably been tilted as shown in FIG. 9 (and FIG. 11A, et al, see below) to provide a bag retention during centrifugation. Nonetheless the functionality remains substantially the same in this embodiment as it was in the embodiment of FIGS. 1–4. A composite fluid still flows out of the central containment area, here designated 42a, to the separation channel, here 50a, where the fluid is separated and the separated components then flow to each respective outlet region 51a, 52a to the collection areas 43a, 44a. Note, dashed lines 53a, 54a shown in FIG. 9 represent either outlet channels or outlet tubing lines (or both) which lead to the respective pockets 43a, 44a. See also solid line versions of channels/tubing lines 53a, 54a in FIG. 10.

Figure 10:
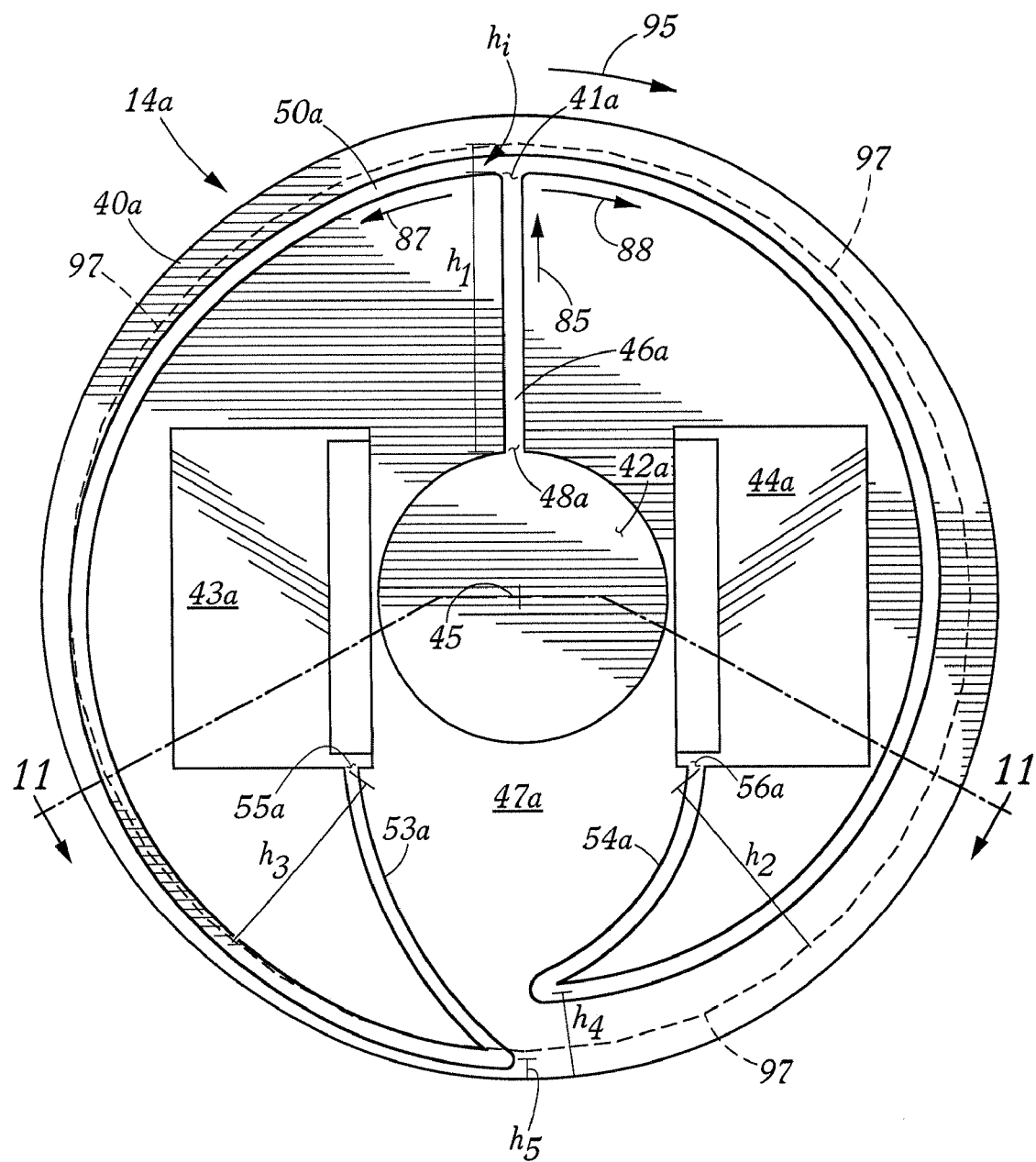
FIG. 10 is a plan view of the alternative rotor/centrifuge of FIG. 9.

This embodiment of FIGS. 9 and 10 does not differ substantially operationally from the embodiments of FIGS. 1–8. Rather, a primary difference would likely be in manufacturing where the rotor 40 of the previous embodiments of FIGS. 1–8 may likely be formed by molding plastic, and the alternative rotor 40a of FIGS. 9 and 10 may not require molding and instead could be formed from sheet materials, such as plastic sheet, either cut and adhesively manufactured into shape, such as in pockets 43a, 44a; or, perhaps by heat shaping, rolling and/or bending into circular or substantially circular walled members like containment area 42a and the peripheral channel 50a.

Thus, pockets 43a and 44a may each have several walls, as shown, including for example, top and bottom walls 43b, 43c and 44b, 44c. Respective side walls 43d, 43e and 44d, 44e are also shown in this embodiment (FIG. 9). Slotted apertures 55a and 56a are shown as preferably formed in respective side walls 43e and 44e. Apertures 55a and 56a cooperate with channels/tubing lines 53a, 54a to provide ingress flow into respective pockets 43a, 44a.

Similarly, respective wall members may be easily formed to create the other primary portions of rotor 40a as shown in FIG. 9. A circular cylindrical wall 62a can form blood containment area 42a and respective radial walls 64a, 65a form radial inlet channel 46a, as do inner and outer circumferential walls 66a, 67a form circumferential channel 50a. A substantially common floor 47a is also shown, see particularly FIGS. 11A–11D.

In operation, this FIGS. 9 and 10 embodiment works as described before, and is rotated about a central axis 45 as shown in FIGS. 10 and 11A–11D. A composite fluid such as whole blood 90 is disposed in a containment area 42a (see FIG. 11B), and when rotor 40a is caused to rotate, the composite fluid flows out of containment area 42a into and through channel 46a to the circumferential channel 50a. The composite fluid is separated into components such as RBCs 91 and plasma 92 (see FIGS. 11C and 11D) in separation area 41a of channel 50a (see FIG. 10). The separated components then flow through respective portions of the channel 50a to their respective collection areas 43a and 44a (see flow arrows 85, 87 and 88 in FIG. 10) in a fashion such as that described for FIGS. 7 and 8 above.

Forward flow is here also caused and maintained by the respective fluid pressure values such that the fluid pressure in and through inlet channel 46a is greater than those in the exit flows in channels 53a and 54a. The inlet pressure is $\rho_1 g_1 h_1$ where $\rho_1$ is, as above, the density of whole blood and $h_1$ is the relative height of the inlet 48a of channel 46a from the exterior reference circle 97 and the relative outlet pressures are $\rho_2 g_2 h_2$ and $\rho_3 g_3 h_3$ (as above) where $\rho_2$ is the density for plasma with a corresponding height $h_2$ to the plasma outlet port 56a, and $\rho_3$ is the density of the RBCs with a corresponding $h_3$ to the RBC outlet port 55a; Note, here also the $h_2$ value may include a modification term related to the $\rho_{RBC} g_{RBC} h_i$ where $h_i$ is the height of the interface (not directly shown in FIG. 10; but see similar interface in FIGS. 7 and 8 above) between the separated components in the separation area 41a. In any event, the $\rho_1 g_1 h_1$ value (with or without an $h_i$ modification) is preferably established to be greater than either of the outlet pressure values $\rho_2 g_2 h_2$ and $\rho_3 g_3 h_3$. This is Equation No. 1 from above. Moreover, here also, the interface is maintained in a desirable location by the equalization of the outlet line fluid pressures such that $\rho_2 g_2 h_2 = \rho_3 g_3 h_3$ (Equation No. 2).

Figure 11A:
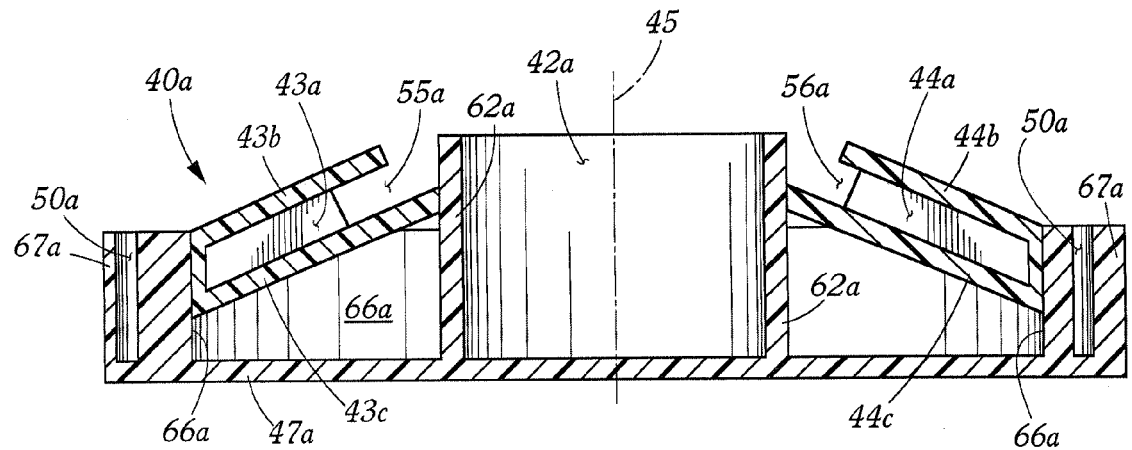
FIGS. 11A, 11B, 11C and 11D are cross-sectional views of the alternative devices of FIGS. 9 and 10 taken along line 11—11 of FIG. 10.
Figure 11B:
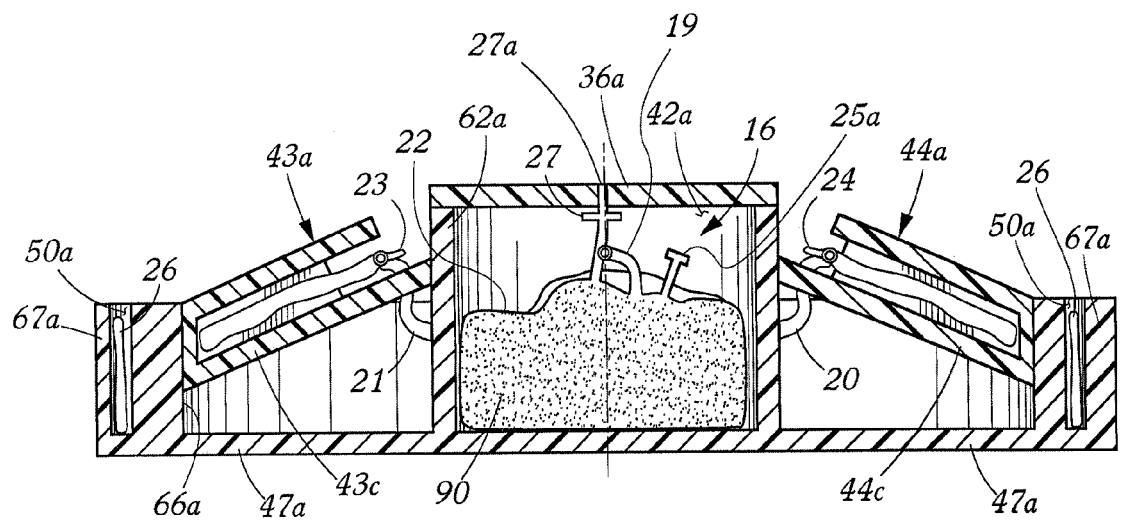
Figure 11C:
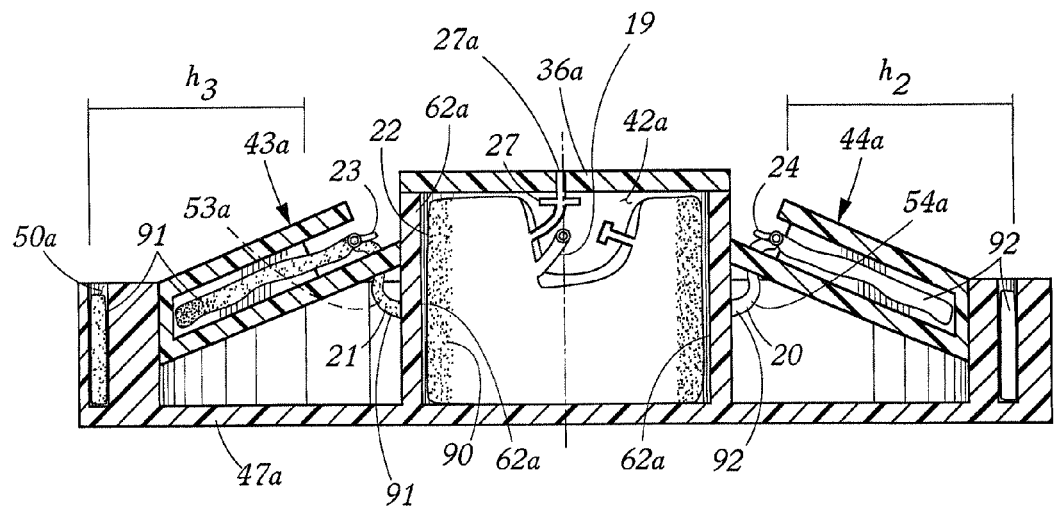
Figure 11D:
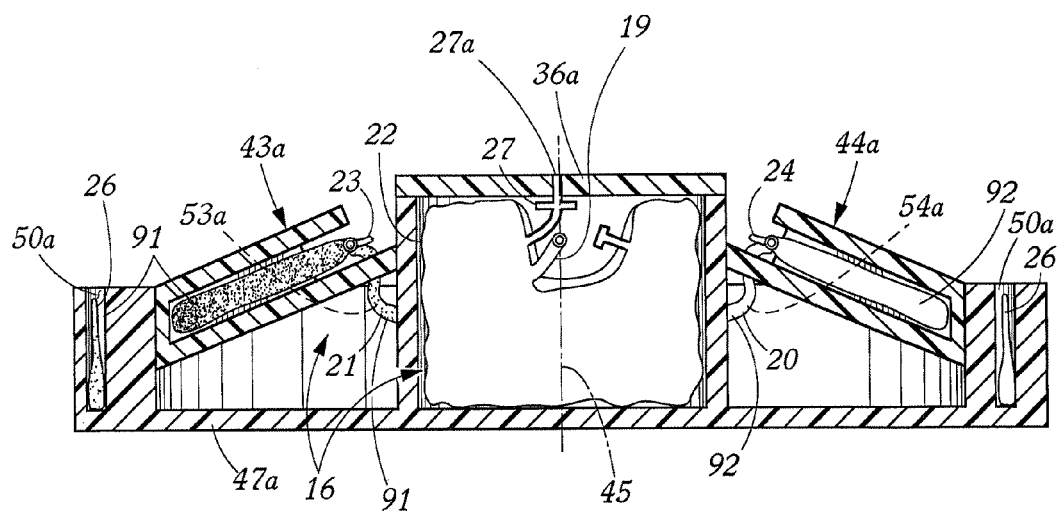

Further facets of the operation can be seen in the cross-sectional views of FIGS. 11B–11D. A tubing and bag set such as set 16 from FIG. 5 may also be used with rotor 40a and thus may be placed into rotor 40a as shown in FIG. 11B. As is depicted here, a substantially full bag 22 may be disposed in receiving area 42a with the empty vessel 26 and bags 23, 24 disposed in their respective receiving areas, vessel 26 in channel 50a and bag 23 in pocket 43a and bag 24 in pocket 44a. Radial tubing line 19 would be disposed in channel 46a (not directly shown) and tubing lines 20, 21 are, as is partially shown in FIGS. 11B–11D, run from the circumferential channel 50a to the respective pockets 43a, 44a. As shown in FIGS. 9 and 11B–11D, no actual receiving channels (see the dashed lines 53a and 54a in FIG. 9) may be necessary for retaining tubing lines 20, 21. Similarly, though not shown as such in FIG. 9, a physical receiving channel 46a with defining walls 64a, 65a may also not be necessary for holding the radial tubing line 19 leading from containment area 42a to channel 50a. Thus, it appears that even certain other interior walls (see e.g., interior channel wall 66a and/or perhaps bottom walls 43c, 44c) may not be necessary either. What is necessary is some structure to retain the circumferentially flowing fluids in the orientations presented in FIG. 10 such that the respective heights, $h_1$, $h_2$ and $h_3$, are maintained relative to each other.

Nonetheless, FIG. 11B depicts the relative rotor 40a and bag set 16 prior to centrifugation. FIG. 11C, then, shows the same combination as in FIG. 11B after centrifugation has begun. The whole blood in bag 22 is forced by the centrifugal forces toward the exterior definition of containment area 42a, also known as the wall 62a. A lid 36a (FIGS. 11B, 11C and 11D) may be used to maintain a vertical upper limit of travel for such whole blood within containment area 42a. Although not shown here, the fluids in containment area 42a could take on a semi-parabolically shaped disposition such, for example, as that shown in FIG. 6B. Note, also as shown in FIGS. 11B–11D, is a passage or structure 27a which is disposed in and/or through lid 36a and which communicates with air vent structure 27 of bag 22 to provide for air ingress into bag 22, particularly as whole blood seeks wall 62a and outflows therefrom. Here also a microorganism filter (e.g. 0.2 micron) may be used to maintain sterility inside the bag 22 and system 16. Returning briefly to FIG. 10, blood flowing out of bag 22 and containment area 42a travels through tubing line 19 and/or channel 46a (not shown in FIGS. 11A–11D) to the channel 50a. See flow arrow 85 in FIG. 10. In channel 50a, the whole blood (or other composite fluid) is separated into its component elements (see separation area 41a, and see FIGS. 7 and 8 described above), and the component elements then flow in channel 50 in their respective directions, see flow arrow 87 for RBCs flowing counterclockwise and see flow arrow 88 for plasma flowing clockwise. These directions (or the opposites) may be used with a clockwise rotation, see arrow 95, of the rotor 40a or with a counterclockwise rotation (not shown). Separated RBCs 91 are shown as they flow in vessel 26 in channel 50a in FIG. 11C. Separated plasma 92 is similarly depicted (though as a substantially clear fluid) in FIG. 11C. Also shown here are the respective flows of separated components, RBCs 91 and plasma 92, through their respective tubing lines 21, 20 (dashed line representations of the would-be channels 53a, 54a are also indicated) to the respective bags 23, 24 inside pockets 43a, 44a. RBCs 91 are shown filling bag 23, as it would under centrifugal forces, to the outside first (as also would the plasma 92 into bag 24). The respective heights $h_3$ and $h_2$ are also shown generally in FIG. 11C.

The completion portion of the centrifugation process is shown in FIG. 11D such that substantially (if not completely) all of the whole blood (or like component fluid) is removed from the bag 22, having flowed therefrom through tubing line 19. Air has preferably substantially filled bag 22 by ingress through vent 27 and aperture structure 27a. Bags 23 and 24 have been substantially filled with respective components, RBCs 91 and plasma 92, with preferably a minute remainder of fluids (or a buffy coat product) in vessel 26 and tubing lines 19, 20 and 21. Rotation of rotor 40a can then be stopped and bag set 16 removed therefrom. Tubing lines 20, 21 can then be heat sealed and/or cut to separate collection bags 23, 24 therefrom for subsequent storage processing and/or use in transfusion (as known in the art).

Note, air an air vent 27 on bag 22 will preferably allow bag 22 to achieve a somewhat cylindrical shape for the composite fluid to seek the wall 62 of area 42 and provide for simplicity in allowing egress therefrom. However, air likely will not, but may have been vented from bags 23, 24 during operation as introduced above; however, as understood, any such vents 27 in bags 23, 24 may then need to be sealed shut after centrifugation for more desirable storage conditions. Note also that subsequent processing (e.g. leukoreduction, filtration, viral inactivation or storage solution addition) prior to storage or use of the separated components may also be desired, and such may be performed preferably after completion of the centrifugation process.

Another set of alternative rotor/separation channel schemes is shown in FIGS. 12–16. A challenge in implementing the RBC/plasma separation device described hereinabove involves single whole blood product scale and associated manufacturing and mechanization. According to the preferred embodiments, the above rotors are designed to accommodate an approximate one whole blood unit or bag 22 with its associated component collection bags 23, 24. A correspondingly-scaled, single unit motor base 12 may then spin one such rotor 40 (or 40a; FIGS. 9a and 10) at a time. As such, this may provide an attractive simple scheme for what is at times referred to as "chairside" separation, i.e., separation at or near the site of the donation of the whole blood unit. However, some operators may prefer and/or some situations may dictate the processing of more than one whole blood unit at a time. Such is provided by the embodiments of FIGS. 12–16.

Figure 12:
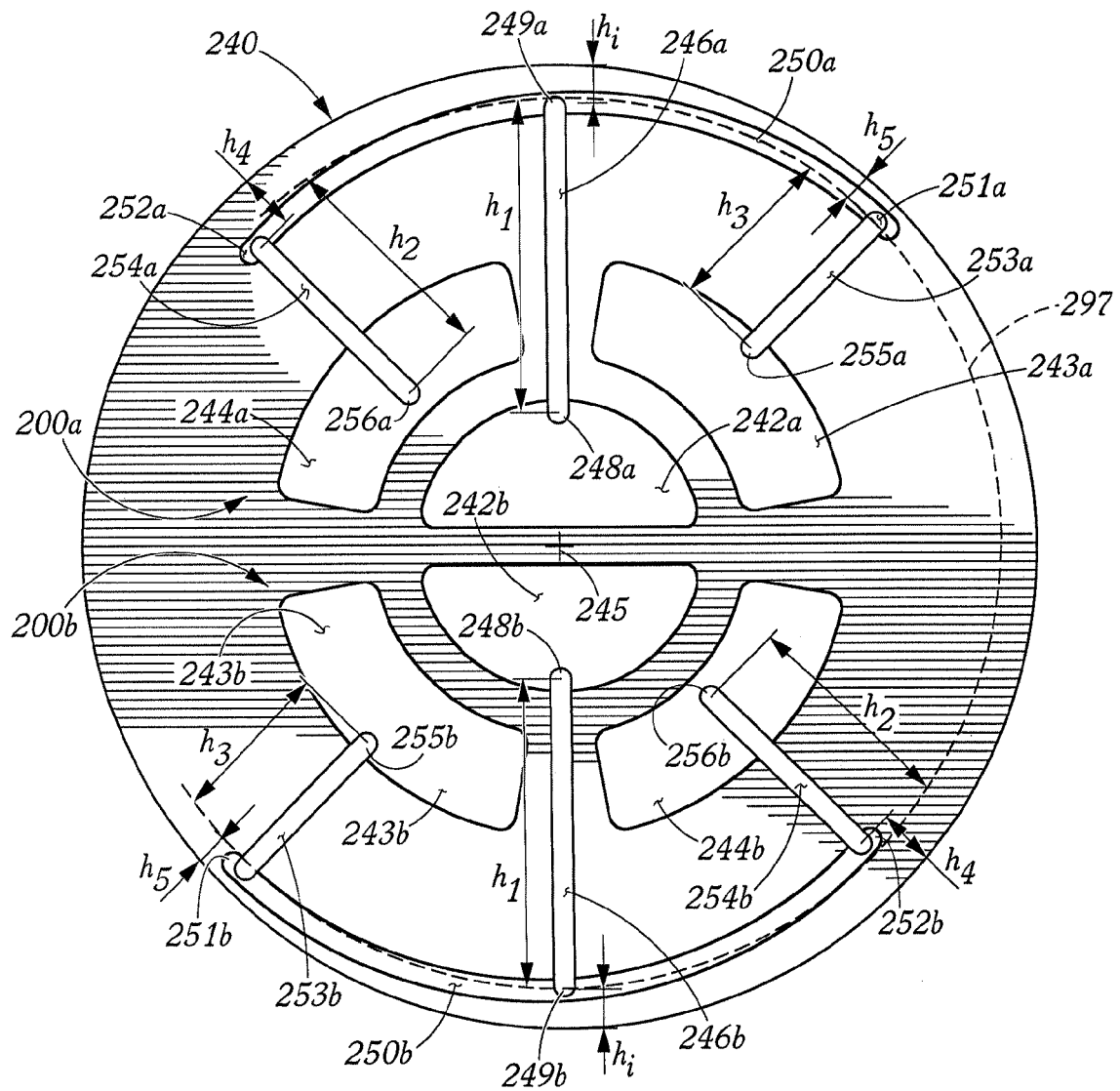
FIG. 12 is a plan view of an alternative rotor according to the present invention.
Figure 13:
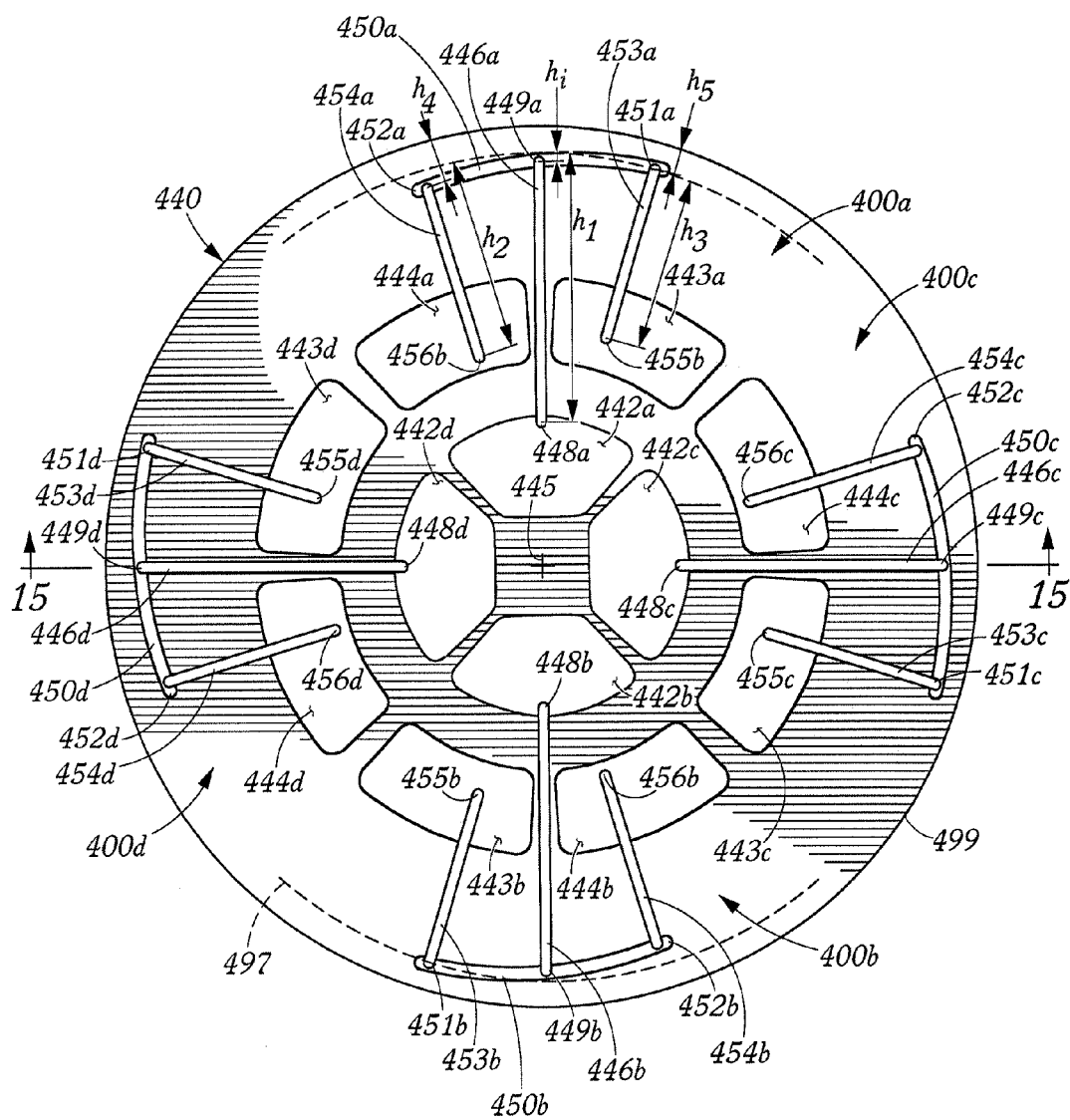
FIG. 13 is a plan view of another rotor alternative according to the present invention.

First, FIG. 12 shows, for example, the incorporation of two discrete processing areas 200a, 200b in/on one rotor 240. FIG. 13, et al. show four such areas 400a, 400b, 400c, and 400d on one rotor 440. Note the respective suffix characters a and b in FIG. 12 and a, b, c and d in FIGS. 13, et al, are intended here to generally indicate and distinguish the similar elements of the distinctive processing areas, e.g. 200a and 200b in FIG. 12 and areas 400a, 400b, 400c and 400d in FIGS. 13, et al. Thus, and in comparison to the elements of the above-described embodiments, the single blood separation pathway 50 (and 50a) of the initially described centrifugation configuration embodiments (see FIGS. 1–4 and 9–10, e.g.) can be divided into two or more tandem, opposing flow pathways 250a and 250b; and 450a, 450b, 450c and 450d as shown, for example, in the respective rotors 240 and 440 of FIGS. 12 and 13. The two flow paths 250a and 250b in FIG. 12 are preferably opposed so as to balance each other by weight distribution in the centrifuge rotor 240 (as are the four paths 450a, 450b, 450c and 450d in the rotor 440, etc.) regardless of the material filling the flow paths, whether the materials are air, blood, or any other fluid. Similarly, other multiple processing area schemes will provide similar fluid balancing (not all shown).

Moreover, in describing the other parts of these alternative configuration embodiments in slightly more detail, FIG. 12 shows in rotor 240 two discrete whole blood containment areas 242a and 242b in which whole blood to be separated will first be disposed. Two red blood cell (RBC) collection areas 243a, 243b and two plasma collection areas 244a, 244b are also included. Two discrete radial inlet channels 246a, 246b are shown as connected between respective whole blood areas 242a, 242b and the corresponding semi-circumferential channels 250a, 250b. Also connected to each of these respective channels 250a, 250b, at either end thereof are respective channels for feeding separated components to the component collection areas 243a, 243b and 244a, 244b. These channels are more specifically the RBC outlet channels 253a, 253b and the plasma outlet channels 254a, 254b. As such, respective outlet channels 253a, 253b feed from the RBC outlet regions 251a, 251b of channels 250a, 250b to the respective RBC collection areas 243a, 243b. In similar fashion, two plasma outlet channels 254a, 254b feed from the plasma outlet regions 252a, 252b to the plasma collection areas 244a, 244b. As will be further described below, similar structural features are also included in other multiple unit processors (see, e.g., FIGS. 13–18 and 19A–19D).

In any event, the principally preferred features hereof are shown by, for example, the disposition of the respective separation channels 250a, 250b such that the respective RBC outlet regions 251a, 251b thereof are disposed radially further outwardly than the respective plasma outlet regions 252a, 252b thereof. Reference circle 297 representing the preferred circular circumference of rotor 240 assists in the demonstration of this feature. This may also be thought of in terms of the channels 250a, 250b being disposed such that they spiral inwardly (relative or about the axis 245) over the whole arc of the channel 250a, 250b (if looked at from RBC outlets 251a, 251b to the plasma outlets 252a, 252b) or at least from the inlet thereto from channels 246a, 246b inwardly to the plasma outlets 252a, 252b. Thus, also, the channels 250a, 250b may be described as spiraling outwardly over the arcs thereof (from the plasma outlets to the RBC outlets) or at least outwardly from the inlets to the channels 250a, 250b (at the intersections 249a, 249b with radial channels 246a, 246b) to the RBC outlets 251a, 251b. Relative to circumference 297, this may be seen by the relationship of $h_4 > h_5$. Note, here also $h_i$, the height of the interface (interface not shown) is preferably between $h_4$ and $h_5$; e.g., $h_i$ is disposed preferably below the outlet represented by $h_4$ and above the outlet represented by $h_5$ (see, e.g., FIG. 8 and description thereof). Additionally, the above described fluid pressure relationships involving the inlet and outlet "heights" (e.g., to inlet ports 248a, 248b and outlet ports 255a, 255b and 256a, 256b) remains desirable in this and other multiple unit embodiments hereafter described. In particular, the forward flow driving relationship is the same here where the inlet fluid pressure is greater than the combination of the outlet fluid pressures, particularly by appropriate height selections; i.e.: $\rho_1 g_1 h_1 > \rho_2 g_2 h_2$, or, $\rho_1 g_1 h_1 > \rho_3 g_3 h_3$ (Equation No. 1).

Here also, any or all of the $\rho g h$ pressure terms may also include summations or correction factors to account for the presence of either gradient densities and/or more than one fluid component (composite or separated component fluid) separated component interface and the density differences associated therewith (see FIGS. 7 and 8 and accompanying descriptions therefor). Similarly, the interface control feature described above also applies to these multi-unit embodiments. Namely, maintaining the outlet fluid pressures in substantially equal balance will keep the interface in a desirable position within the separation channels 250a, 250b. In particular this is accomplished by selecting the respective outlet heights such that:

$$\rho_2 g_2 h_2 = \rho_3 g_3 h_3 \quad \text{(Equation No. 2).}$$

This provides interface control. Note, the respective h values for the respective channel heights are preferably (but not necessarily) equal to maintain balance of the overall rotor. For example, the respective $h_1$'s for the respective inlets 248a, 248b are preferably (but not necessarily) of the same value. Similarly, the $h_2$'s for the plasma outlets 256a, 256b are preferably equal, as are the respective $h_3$'s for the RBC outlets 255a, 255b.

As introduced above, FIG. 13 shows a similar multi-unit embodiment with a rotor 440 which here has four processing areas generally designated 400a, 400b, 400c and 400d as will now be described in more detail. Note the corresponding elements from the respective four separate processing areas 400a–d have discrete suffixes a, b, c and d after each respective identification numeral to thereby identify and distinguish the discrete but similar elements of the discrete processing areas 400a–d.

As such, there are four substantially centrally disposed whole blood receiving/containment areas or pockets 442a–d which feed into four respective inlet channels 446a–d at the inlet ports 448a–d thereto. Channels 446a–d then feed into peripheral channel portions 450a–d at the inlet ports 449a–d. Channels 450a–d then communicate with respective RBC and plasma outlet channels 453a–d and 454a–d via respective outlet ports 451a–d and 452a–d. Outlet channels 453a–d then communicate to respective RBC and plasma collection areas or pockets 443a–d and 444a–d.

Figure 14:
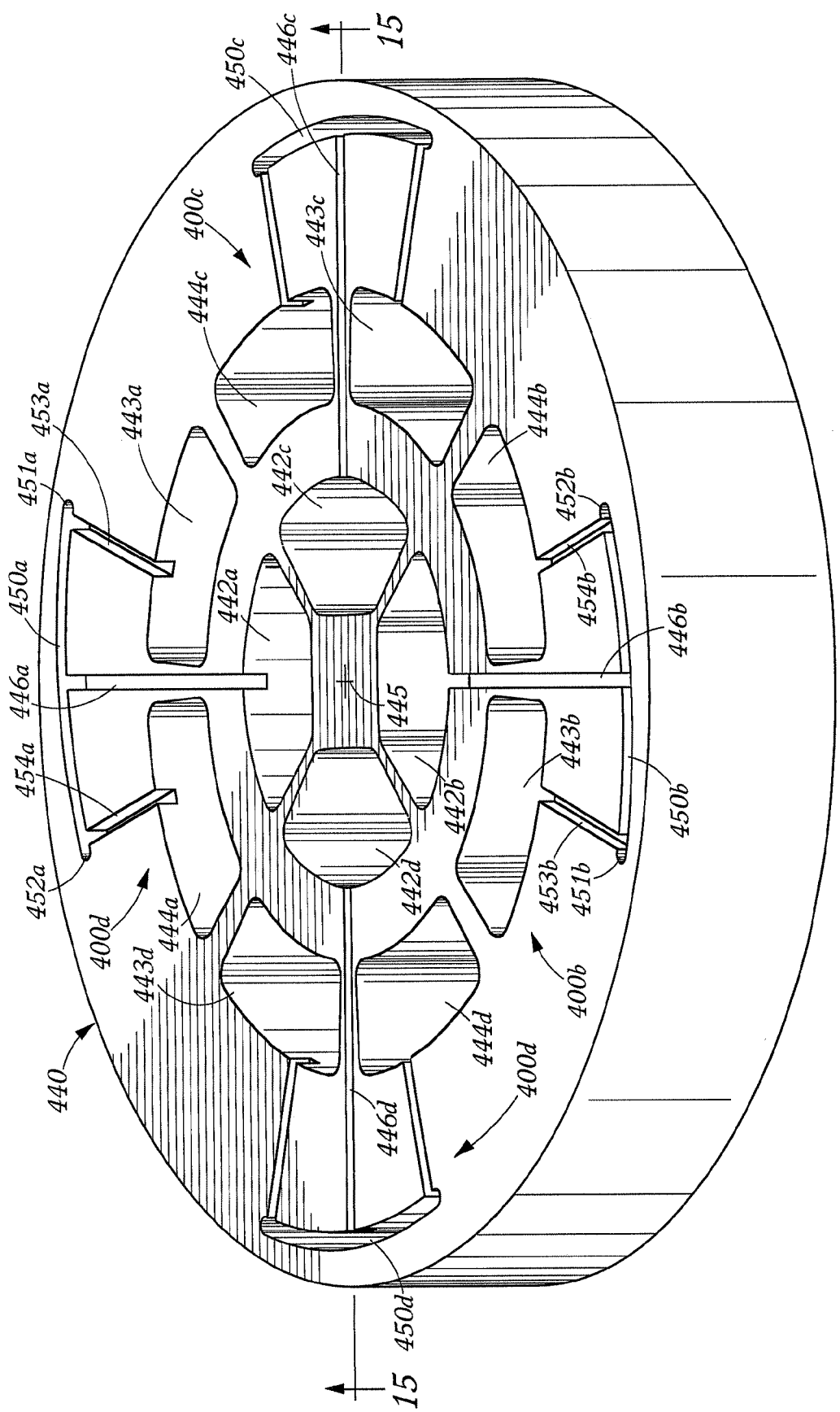
FIG. 14 is an isometric view of a rotor/centrifuge of the separation device embodiment of FIG. 13.

Outlet ports 455a–d and 456a–d provide this ultimate communication. FIGS. 14 and 15 provide depth for further appreciation of the preferred discrete elements hereof.

Note here also that the relative distances or "heights" of the inlet and outlet ports, particularly inlet ports 448a–d and RBC and plasma outlet ports 455a–d and 456a–d are the drivers and controllers of the separation processing provided hereby. More particularly, the inlet height $h_1$ is chosen such that the fluid pressure therein, $\rho_1 g_1 h_1$ is greater than either of the fluid pressures in the outlet lines $\rho_2 g_2 h_2$ and/or $\rho_3 g_3 h_3$ (see Equation 1, above). And here also, there may be a modification desired for the interface (if it occurs along this height) such that any density RBCs at a height of $h_i$ can be used to provide more accuracy in the determination of the fluid pressure in or otherwise relative to the inlet line, e.g., in or near 446a–d.

The interface control heights $h_2$ and $h_3$, (also known as the outlet heights) are thus also similarly chosen here such that the respective outlet fluid pressures are substantially equal. See e.g., Equation No. 2; i.e., $\rho_2 g_2 h_2 = \rho_3 g_3 h_3$. Preferably here also, the respective outlet heights $h_4$ and $h_5$ from the baseline, e.g., the circumference 497 of rotor 440, are established such that $h_4 > h_5$; and also preferably such that the interface height $h_i$ is disposed therebetween; e.g. In is below the port measure by $h_4$ and above the port measured by $h_5$.

As above, these embodiment rotors may be manufactured using any of various methods including, for example, molding in plastic. The molds could be in one or more parts to arrive at the configurations shown or the like. Alternative processes and materials may also be used including the use of formable sheet materials as in the embodiments of FIGS. 9, 10 and 11A–11D in the production of non-molded multi-unit embodiments (not shown).

Moreover, as the scale increases, e.g., as the number of processing areas, e.g., 400a–d; and/or as the radius from the central axis, e.g., axis 445 in FIG. 13, increases to the circumference, as in circumference 499 in FIG. 13, then larger driving centrifuge motor bases (not shown) will likely need to be used. Nonetheless, it appears that a multi-unit rotor such as rotor 440 of FIGS. 13–15 (or other quantity units from two up to perhaps six, eight, twelve, or even more units) may be made to replace the rotor of an existing bucket or cup centrifuge machine; such machines typically already being used in blood banks for blood component separation. Thus, existing drive machinery may be used to generate the forces desirable for separation and flow (e.g., high revolutions per minute (RPMs) and/or large g forces such as up to perhaps 5000 g's (5000× gravity), for an example).

A simplified, schematic representation of a spindle receptacle 500 to demonstrate one means for providing the operative interface of a rotor 440 with the drive shaft or spindle of a pre-existing rotor is shown in FIG. 15.

Figure 16:
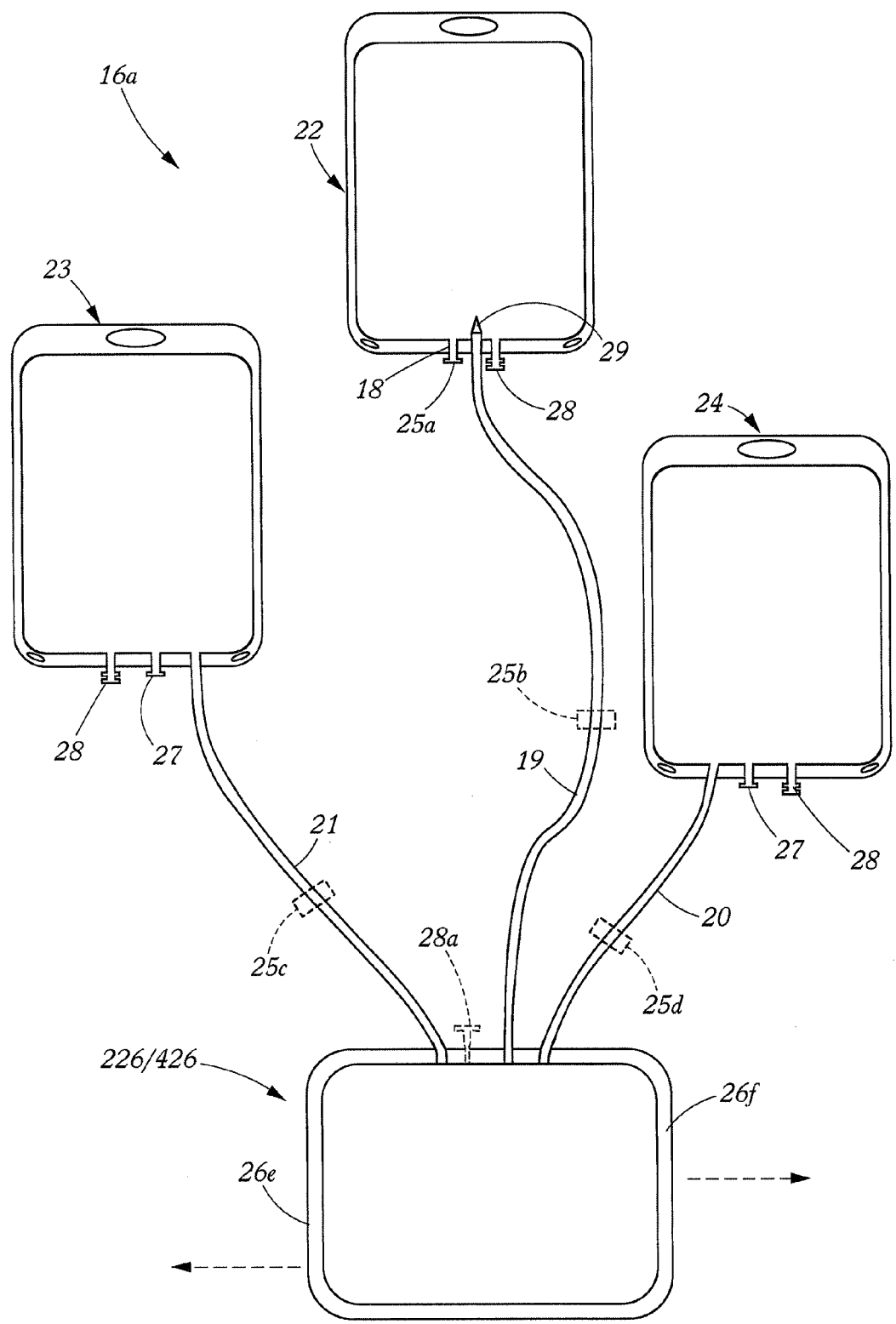
FIG. 16 is a plan schematic view of a tubing and bag system for use in the alternative embodiments of the present invention shown in FIGS. 12–15.
Figure 17:
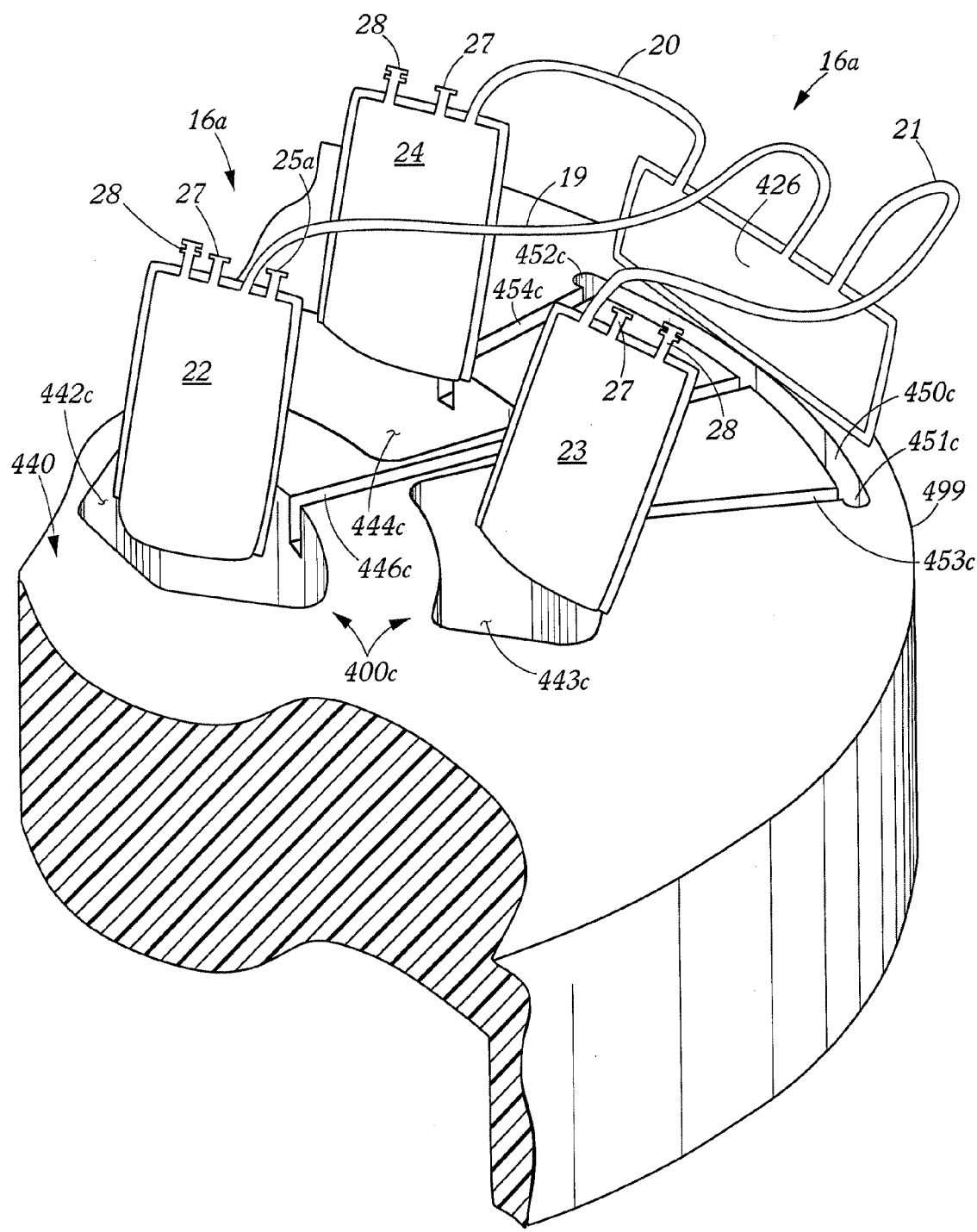
FIG. 17 is an exploded partial isometric view of the alternative embodiment of the rotor/centrifuge of FIGS. 13–15 with a tubing and bag system according to FIG. 16.

Among various advantages of these embodiments, one may be found in the tubing and bag set 16a which may be used herewith as shown, e.g., in FIG. 16. The tubing and bag set 16a differs very little from the bag set 16 shown and described relative to FIG. 5, above. For example, there remain three primary bags; a composite fluid/whole blood bag 22 and two separated component bags 23, 24 (RBCs collected in bag 23, and plasma in bag 24) with associated tubing line connections 19, 20 and 21 emanating therefrom. The distinction lies primarily in the separation vessel 226/426, here, to which the tubing lines 19, 20 and 21 are connected. Preferably, vessel 226 is a bag also made in the same fashion and from the same types of materials as the other bags 22, 23 and 24. (Note, as introduced above, a bag was suggested as an alternative vessel 26 for the embodiment of FIG. 5 as well). Nevertheless, vessel 226/426 may be shorter (or longer) and/or perhaps wider (or thinner) and/or may have less (or more) volume than any of the other bags, depending primarily on the rotor configurations chosen, e.g., the length and width of the separation channel 50, 50a, 250 or 450 or otherwise as may be desired. For example, if the edges 26e, 26f (FIG. 16) were disposed in a wider disposition (see dashed line arrows), then the bag/vessel 226/426 may be more elongated even so far as to be adapted to wrap around a rotor such as rotor 40 or 40a (e.g., FIGS. 2–4 and 9–11A).

Further, it may be desirable to use vessel 226 (or 26, or 426 (see FIG. 17)) to retain for collection and subsequent processing and/or use the buffy coat (white blood cells and platelets) which generally rides on the interface between the separated and continuously separating RBCs and plasma. An optional access/connection device 28a is shown in dashed lines in FIG. 16 to provide an option for access to the contents of vessel 226/426 after the centrifugation process. Vents 27 and/or access devices 28 are also shown on the other bags 22, 23, 24 as may be desired. Note, though not shown in FIG. 16, a vent 27 is preferably connected to bag 22. Also, as shown in FIG. 16, the donor access tubing line 18 is shown as preferred sealed and cut after a completed whole blood unit donation as introduced above (bag 22 thus being full of whole blood). The seal and cut line 25a is shown here. Further, dashed line seal and cut areas 25b, 25c and 25d are also shown here as may represent the preferred seals and/or cuts of lines 19, 20 and 21 after centrifugation. Multiple other tubing line cuts and/or seals may also be used. A frangible connector 29 is also shown schematically in bag 22 in FIG. 16 which may be used to provide an initially closed off fluid communication through tubing line 19 until connector 29 is broken to thereby allow fluid communication from bag 22 into and through tubing line 19. Alternative flow stoppage members (not shown) could also be used here (or on the other tubing lines 20, 21, e.g.), such as slide or roller clamps or hemostats or the like, e.g.

Loading of an exemplary set 16a into an exemplary processing area 400c is shown in Fig. In particular, it can be seen that a composite fluid bag 22 is disposed to be positioned in containment or receiving area 442c, with its associated tubing line 19 being disposed to be positioned in transport channel 446c. The collection bags 23, 24 are likewise positioned to be set within their respective collection areas 443c and 444c with their associated tubing lines 21, 20 being disposed to be positioned within respective channels 453c and 454c. Separation vessel 426, here, is shown as it will be positioned in the corresponding peripheral separation channel 450c.

Figure 18:
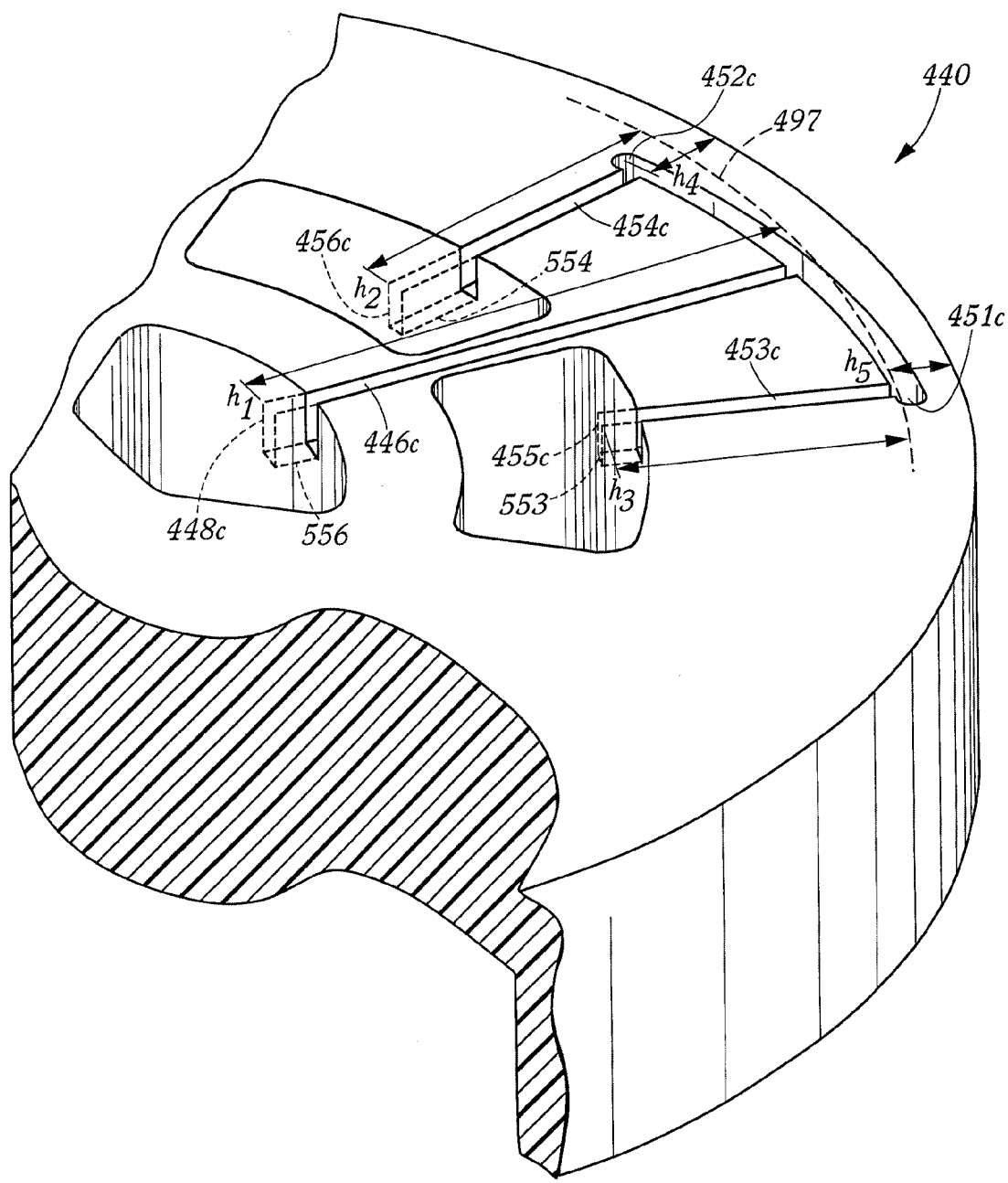
FIG. 18 is a partially isometric view of a rotor alternative as in the embodiment of FIG. 17.

As shown in more detail in FIG. 18, an optional extension member 554 (dashed lines in FIG. 18) may be used to fix the inward extension of the channel 454c, here, to ensure the proper length or height of the fluid pressure term corresponding thereto. Thus, here height $h_2$, measured from the dashed line reference 497, may be assured by the extension member 554. Similar extension members 556 and 553 may be used to fix the respective heights for the inlet fluid pressure value in channel 446c i.e., height $h_1$, and/or in the RBC outlet fluid pressure in channel 453c via height $h_3$. Though not shown in FIGS. 12–15, 17 or 18, lips or ledges (such as ledges 60, 70 in FIGS. 6A, 6B and 6C) may also be used in these multi-unit embodiments to retain fluids within the respective areas and/or channels. A lid (see lid 36; FIGS. 1 and 4) may also be used for this purpose in these multi-unit embodiments.

Figure 19A:
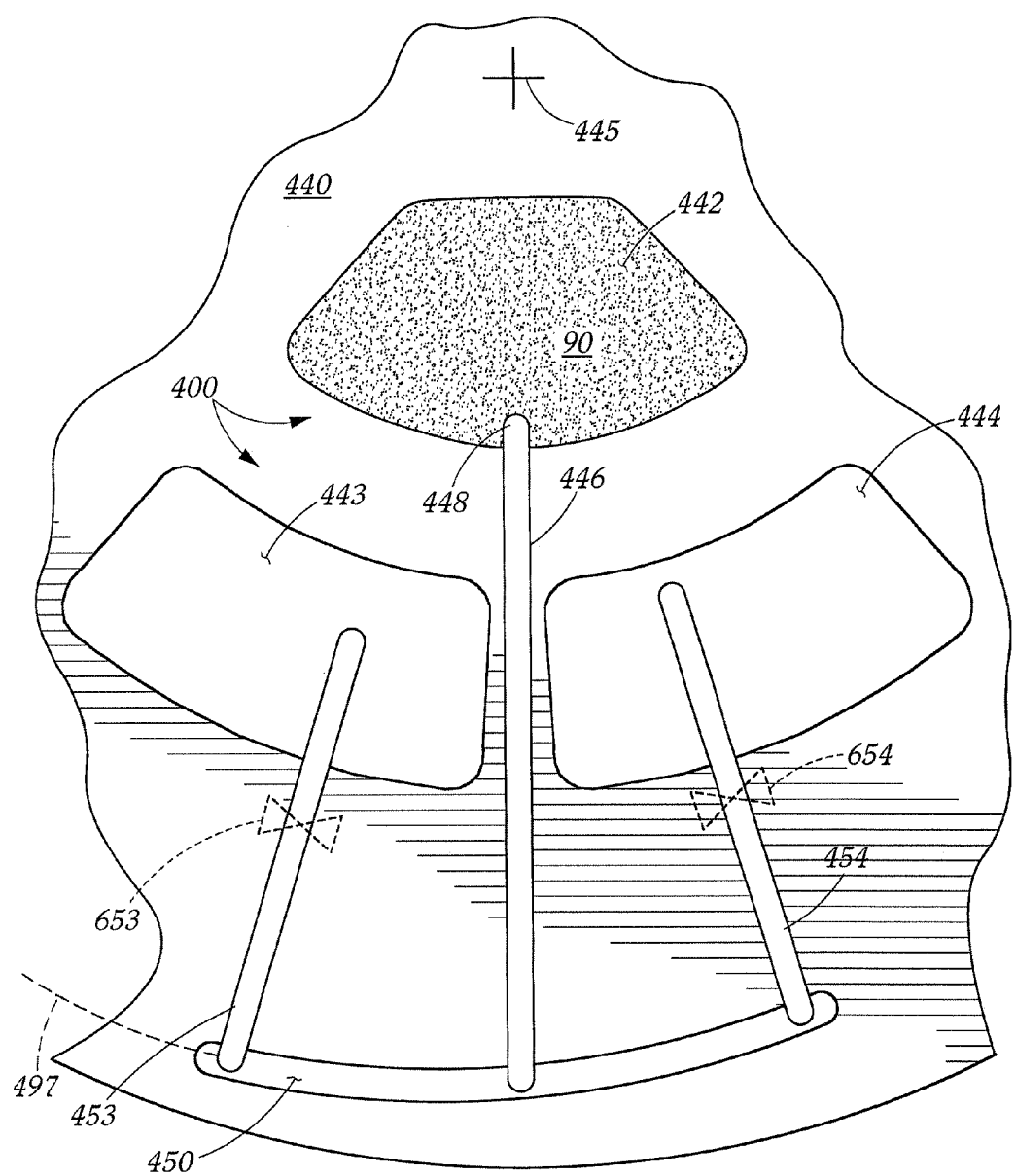
FIGS. 19A, 19B, 19C and 19D are partial plan views of the alternative embodiment of the rotor/centrifuge of FIG. 13 shown in use.

In any case, a preferred process using a processing area 400 is shown in FIGS. 19A–19D. For example FIG. 19A shows the composite fluid 90 disposed in the generically referenced containment area 442. As introduced above, a bag set is not necessary, even if desirable, and thus will not be described relative to FIGS. 19A–19D (however, FIG. 19A would correspond to the point immediately after which the bag set 16 or 16a (see FIG. 17) with a full whole blood bag 22 will have been loaded into the containment and other associated areas 442, 443, 444, and 450 of a separation area 400). If a flow stoppage member or valve (such as a frangible connector 29, see FIG. 16) is used at the port area 448 between containment area 442 and channel 446; this member is then opened (or the frangible 29, broken) to permit flow into the channel 446. Note, shown in dashed lines in FIG. 19A are optional clamps or valves 653 and 654 disposed in or adjacent channels 453, 454 and which may be used to ensure no flow conditions in channels 453, 454 until desired, as for example, until a sufficient rotational speed has been achieved. These may thus be centrifugal clamps which may be disposed on the rotor 440 and may be automatically activated by the achievement of a particular minimum rotational speed of rotor 440. Alternatively, these clamps may be manual (typical pre-rotation activation) or automated by other mechanical and/or electrical means to open and/or close during (or before or after) rotation. Nonetheless, FIG. 19A shows the system after set-up and prior to rotation.

Figure 19B:
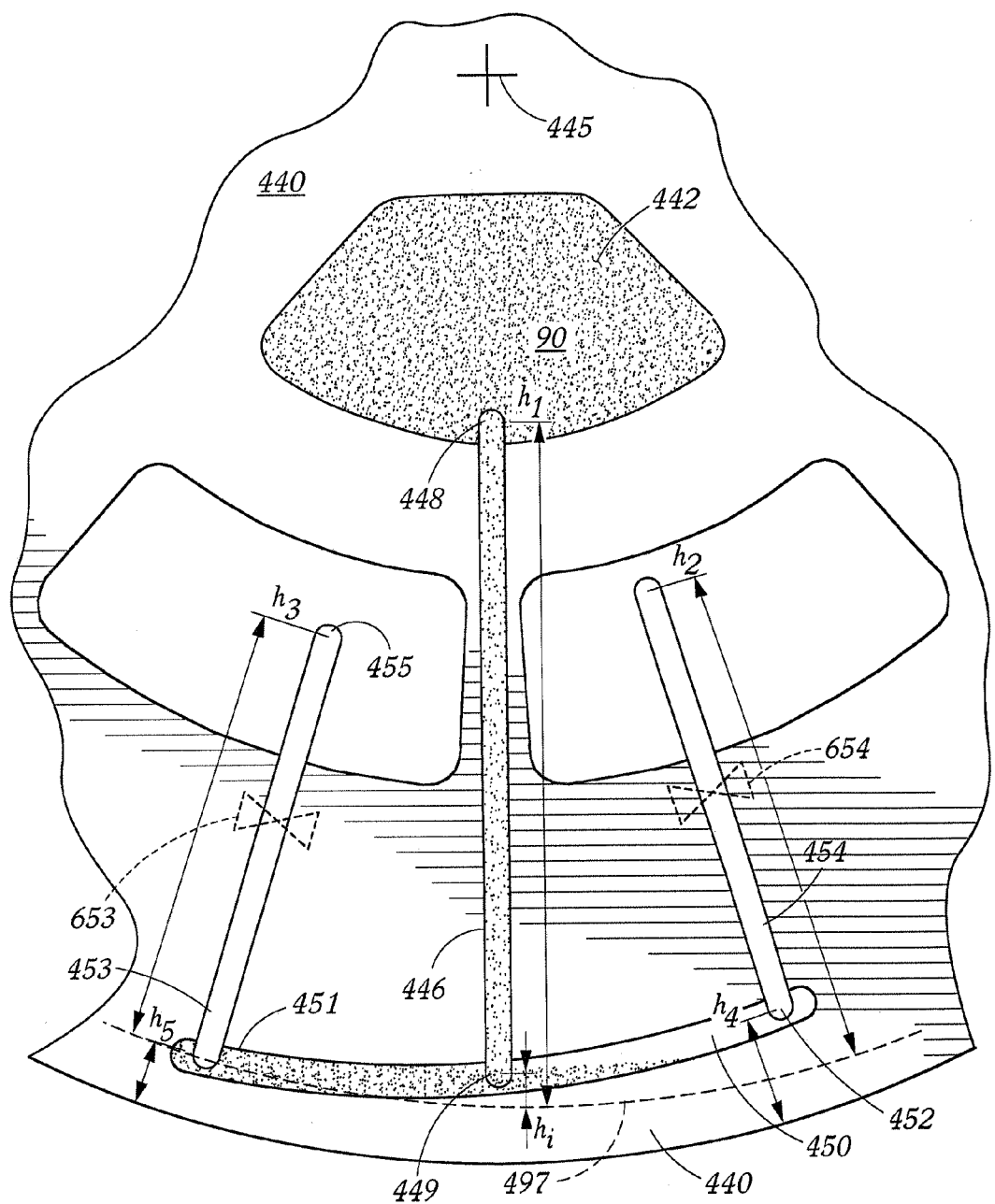

FIG. 19B then shows the initial flow condition when rotation of the rotor 440 has begun about the axis 445. Flow has also begun out of area 442 through port 448 and into channel 446. This flow continues then down channel 446 into the peripheral separation channel 450 via the port area 449. Separation of the heavy and lighter phase components from the composite fluid is shown as it begins here in channel 450. The interface depicted at the height $h_i$ demonstrates the separation. Separated components may then begin their respective flows up the respective channels 453, 454, although this flow may not be allowed by the optional clamping members 653, 654, until a predetermined desirable rotational speed has been reached. Thus, FIG. 19B could represent a sort of flow initiation, separation commencement and or stasis during the transition from zero or low revolutions per minute (RPMs) to the high RPMs here ultimately desired.

Figure 19C:
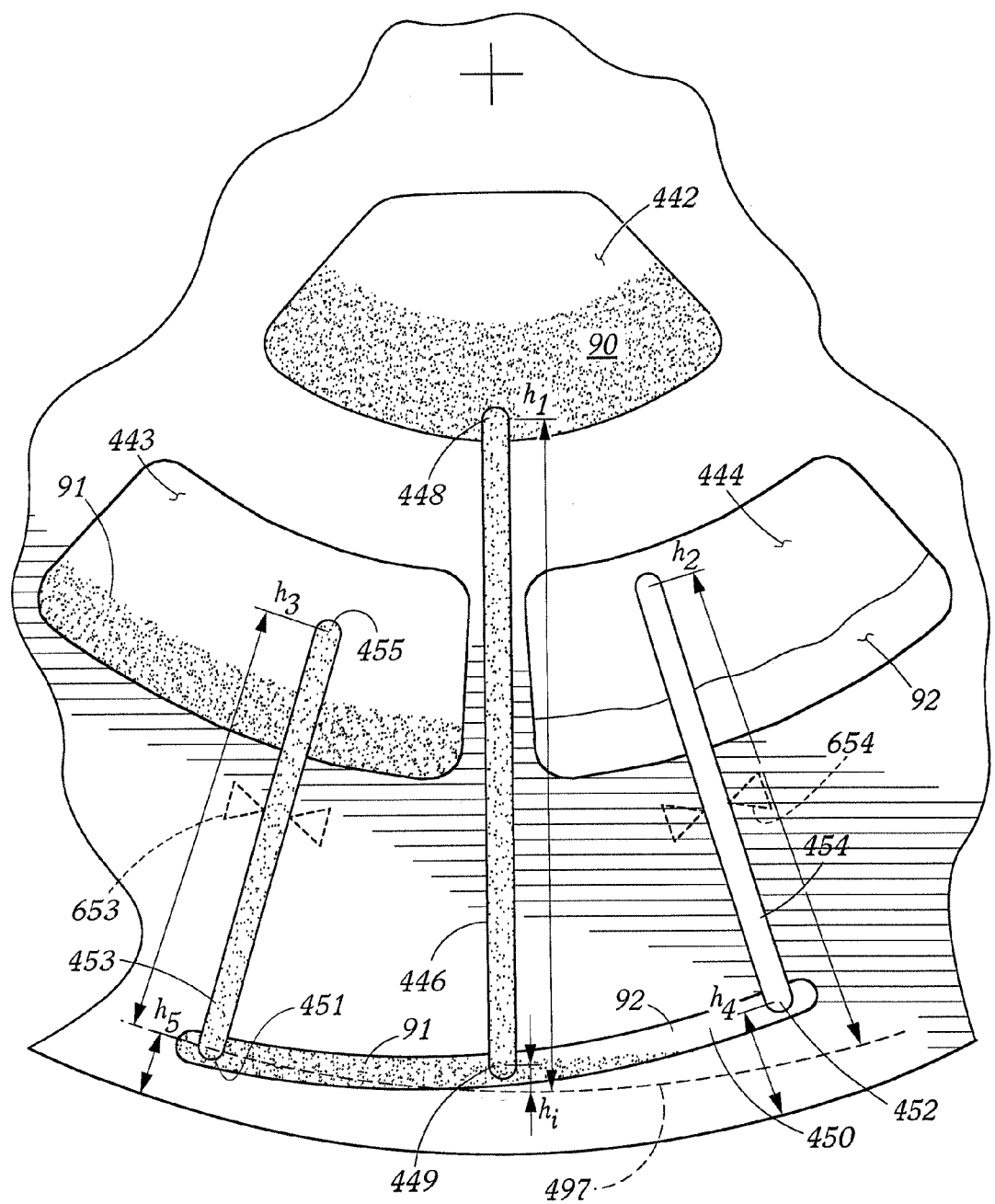
Figure 19D:
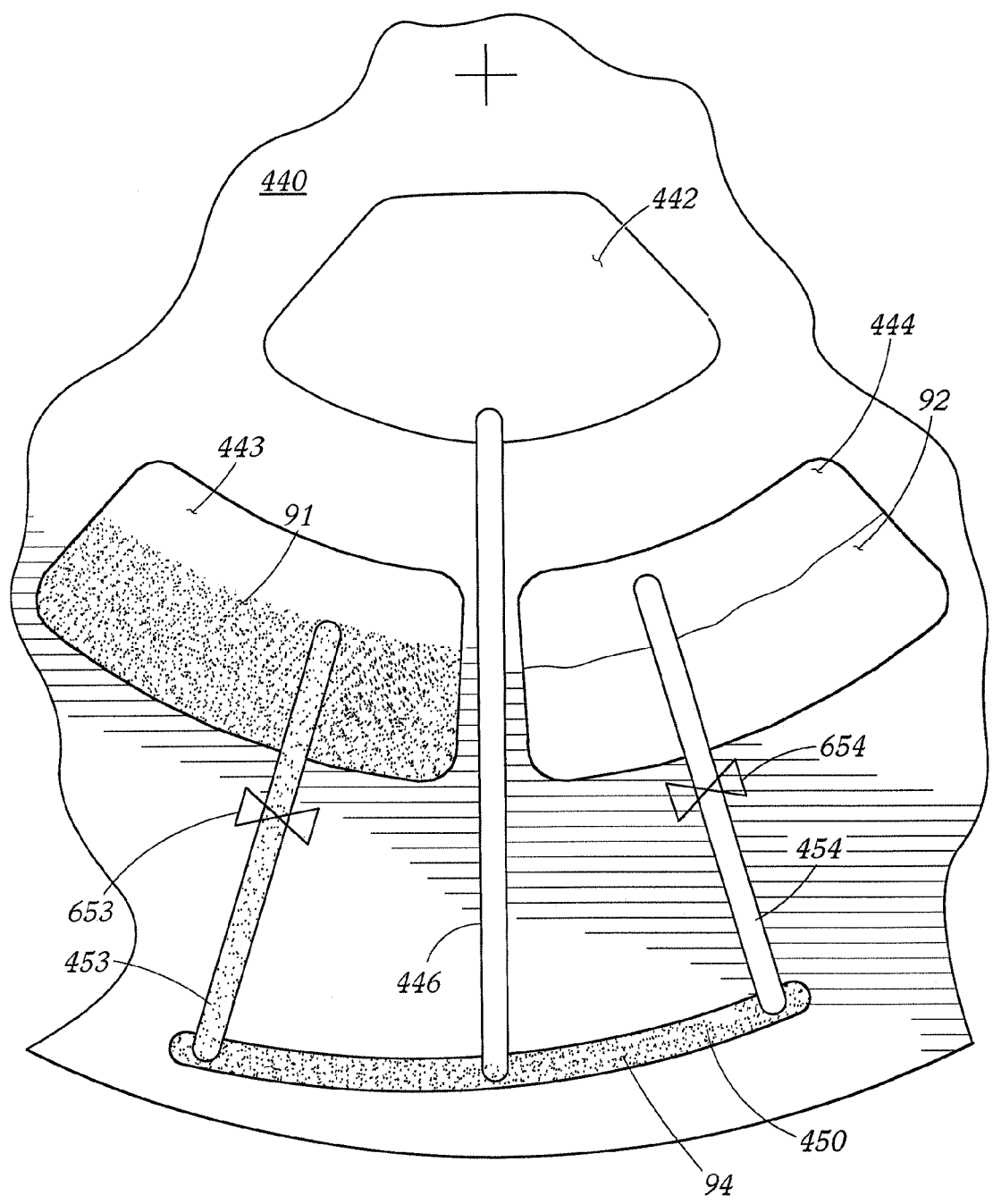

FIG. 19C, on the other hand, represents the higher RPM situation where a continuous flow state (if used, the centrifugal flow clamps 653, 654 are now open) of separated components 91, 92 flowing up from channel 450 through respective outlet channels 453, 454 to the respective collection areas 443, 444. Continuously also, the composite fluid 90 flows out of the containment area 442 through the channel 446 to the separation channel 450. The $\rho_i g_1 h_1 \rho_2 g_2 h_2$ and/or $\rho_1 g_1 h_1 \rho_3 g_3 h_3$ (Equation No. 1) relationship provides the continuous forward flow here also. Thus, as above, $h_i$ to inlet port 448, $h_3$ to port 455 and $h_2$ to port 456 are the chosen forward flow variables. Separation into respective heavier and lighter phases then also continuously occurs in channel 450; however, the interface remains at the same height $h_i$ and as a general concept, the buffy coat (white blood cells and platelets) stay in the separation channel 450 riding on the interface. The $\rho_2 g_2 h_2 = \rho_3 g_3 h_3$ (Equation No. 2) relationship is used here also to maintain the interface at the $h_i$ level. The $h_2$ and $h_3$ values here being the selectable quantities. Similarly, and also as was described above, the channel 450 is offset in a sort of semi-spiraled fashion such that $h_4$ is greater than $h_5$ ($h_4 > h_5$). Then, once the composite fluid 90 has emptied out of the containment area 442, the rotation of rotor 440 may be stopped and also stopped would be the flows in the channels 446, 453 and 454. This situation is shown in FIG. 19D. Indeed, if centrifugal clamps 653, 654 are used, these may be disposed to automatically close as the RPMs of rotor 440 reduce to a certain level. This would ensure no backward flow in channels 453 and 454 and thus no loss of product from the collection areas 443, 444. An optional clamping element (not shown) may also be engaged on/in channel 446, as well. Then, when the rotor 440 is stopped, the respective separated components 91, 92 may be removed from their respective collection area 443, 444. Bags 23, 24 (not shown in FIGS. 19A–19D) would assist in this removal, and the associated tubing lines 21, 20 (also not shown in FIGS. 19A–19D) could then be cut (see the cut areas 25c, 25d in FIG. 16), so the component products 91, 92 may then be stored or subjected to further processing (pathogen inactivation, leukoreduction, filtration and/or storage solution addition, et cetera) or used in transfusion or otherwise. A buffy coat vessel 426 (also not shown in FIGS. 19A–19D; but see FIG. 16) may also be removed from the separation channel 450 and the contents 94 thereof further processed to extract, for example, platelets or other buffy coat components therefrom for further use as may be desired. Access to these contents in such a vessel 426 (or 226, see FIG. 16) could be through a connection device 28 as described for optional use in FIG. 16 and as would be used on the other bags 22, 23 and/or 24. If a bag and tubing set 16a is used, then the remaining non-storage or further processing bags/tubing lines (e.g., bag 22, tubing lines 19, 20 and 21) may then be removed from rotor 440 and discarded as these are preferably disposable after use. Use of such a pre-sterilized disposable set would then enable the rotor to be used repetitively again and again without the need for re-sterilization thereof after each use. It would also alleviate an additional alternative need for manufacturing disposable rotors.

Again, multiple units may be simultaneously processed in this fashion using a rotor 440, for example, disposed preferably within a pre-existing centrifuge device, particularly one with removable, replaceable/substitutable rotors. The multiple unit bag sets could then be handled in the same or a similar fashion to that described from FIGS. 19A–19D.

Other variations (not shown) are also possible including numerous options such as, but not limited to, processing unit quantities and/or structural placements of various containment and/or collection areas and/or channels on the respective rotors and/or relative to each other. Methodology options also abound. Hence, these and various further modifications, adaptations and variations of the structure and methodology of the present invention will become apparent to those skilled in the art without departing from the scope or spirit of the present invention. It is intended that the present invention cover all such modifications, adaptations and variations as limited only by the scope of the following claims and their equivalents.

The invention claimed is:

1. A method for separating a composite fluid into component parts comprising:
   providing a rotor configuration having:
   a rotor that includes
   a composite fluid containment area;
   a fluid inlet channel having an inlet height;
   a peripheral fluid separation channel having a first end, a second end and a central section;
   first and second separated fluid outlet channels; and
   first and second separated component collection areas;
   wherein said inlet channel is disposed in fluid communication with said fluid containment area; and wherein said peripheral separation channel is disposed in fluid communication with said fluid inlet channel in said central section of said separation channel and with said first separated fluid outlet channel adjacent said first end of said separation channel, and with said second separated fluid outlet channel adjacent said second end of said separation channel; and wherein said first and second separated fluid outlet channels are disposed in fluid communication with said first and second separated component collection areas, respectively; and wherein said inlet channel and said first and second separated fluid outlet channels also have respective inlet and first and second outlet heights, said first height being less than said second height, and loading a composite fluid into the composite fluid containment area of said rotor configuration; and rotating said rotor configuration to separate said composite fluid into its component parts.

2. A method according to claim 1 that further includes collecting said separated components.

3. A method according to claim 1 that further includes automatically driving the flow through said separation channel.

4. A method according to claim 1 that further includes automatically shutting off the flow through said separation channel.

5. A method according to claim 1 that further includes automatically readjusting the flow in and through said separation channel by automatically equalizing fluid pressure in the first and second separated fluid outlet channels.

6. A method according to claim 1 which further includes which further includes collecting said separated components and clamping the flow out of said separation channel prior to said step of collecting said separated components.

7. A method according to claim 6 that further includes automatically centrifugally clamping the flow out of said separation channel until a preselected rotational speed is achieved.

8. A method according to claim 6 that further includes automatically centrifugally clamping the flow out of said separation channel after collection of said separated components when a preselected rotational speed is no longer achieved.

9. A method according to claim 6 that further includes automatically capturing an intermediate phase component in said separation channel by clamping the flow out of said separation channel after collection of said first and second separated components when a preselected rotational speed is no longer achieved.

10. A method according to claim 1 that further includes: using a disposable bag and tubing set within said rotor configuration.

11. A method according to claim 1 wherein said separation channel is semi-spiraled about an axis of rotation of said rotor.

12. A method according to claim 11 wherein said first end of said separation channel has a first separation channel height and said second end of said separation channel has a second separation channel height and said first separation channel height is less than said second separation channel height.

13. A method according to claim 12, further comprising rotating said rotor in a selected rotational direction and wherein said first end of said separation channel is behind said inlet channel with respect to said selected rotational direction, whereby relatively denser component parts of said composite fluid tend to flow against said rotational direction towards said first end.

14. A method according to claim 1 wherein said first collection area is disposed radially inwardly from said separation channel and between said inlet channel and said first outlet channel and wherein said second collection area is disposed radially inwardly from said separation channel and between said inlet channel and said second outlet channel.

15. A method according to claim 14 wherein said collection areas comprise pockets, said pockets being tilted radially downwardly and outwardly from an axis of rotation of said rotor.

16. A method according to claim 1 wherein said rotor further comprises at least one extension extending from at least one of said outlet channels into the collection area of said at least one channel, said extension having a fixed end connected to said at least one channel and a free end in said collection area, the height of said at least one channel being determined with respect to said free end of said extension.

17. A method according to claim 1, wherein said rotor further comprises a plurality of processing areas, each processing area having a composite fluid containment area;

a fluid inlet channel having an inlet height;

a peripheral fluid separation channel having a first end, a second end and a central section;

first and second separated component outlet channels; and first and second separated component collection areas;

wherein said inlet channel is disposed in fluid communication with said fluid containment area; and wherein said peripheral separation channel is disposed in fluid communication with said fluid inlet channel in said central section of said separation channel, and with said first separated fluid outlet channel adjacent said first end of said separation channel, and with said second separated fluid outlet channel adjacent said second end of said separation channel; and wherein said first and second separated fluid outlet channels are disposed in fluid communication with said first and second separated component collection areas, respectively; and wherein said first and second separated fluid outlet channels also have respective first and second heights, said first height being less than said second height, each of said processing areas being symmetrically disposed about an axis of rotation of said rotor.

18. A method according to claim 17 comprising at least four processing areas.

19. A method according to claim 18 wherein each peripheral separation channel comprises a semi-spiraled arc.

20. A method according to claim 17, each processing area further comprising at least one extension extending from at least one of said outlet channels into the collection area of said at least one channel, said extension having a fixed end connected to said at least one channel and a free end in said collection area, the height of said at least one channel being determined with respect to said free end of said extension.

21. A method according to claim 20, each processing area further comprising an extension extending from each of said outlet channels.

22. A method according to claim 21 wherein each collection area has a central section and an outlet channel connects to said collection area in said central section.

* * * * *